United States Patent
Rekaya et al.

(10) Patent No.: US 9,956,347 B2
(45) Date of Patent: May 1, 2018

(54) ADD-ON GRIP AND ACTUATION-SLEEVE FOR A PEN-TYPE DRUG INJECTION DEVICE

(71) Applicant: SANOFI-AVENTIS DEUTSCHLAND GMBH, Frankfurt am Main (DE)

(72) Inventors: Naceur Rekaya, Warwickshire (GB); Paul Richard Draper, Worcestershire (GB); David Aubrey Plumtre, Worcestershire (GB); Robert Veasey, Warwickshire (GB); Daniel David Higgins, Warwickshire (GB); Matthew Jones, Warwickshire (GB); Michael Bainton, Warwickshire (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 336 days.

(21) Appl. No.: 14/770,851

(22) PCT Filed: Mar. 10, 2014

(86) PCT No.: PCT/EP2014/054533
§ 371 (c)(1),
(2) Date: Aug. 27, 2015

(87) PCT Pub. No.: WO2014/139921
PCT Pub. Date: Sep. 18, 2014

(65) Prior Publication Data
US 2016/0008546 A1    Jan. 14, 2016

(30) Foreign Application Priority Data
Mar. 13, 2013  (EP) ..................... 13159056

(51) Int. Cl.
*A61M 5/31*    (2006.01)
*A61M 5/315*   (2006.01)
(Continued)

(52) U.S. Cl.
CPC ........ *A61M 5/3137* (2013.01); *A61M 5/3129* (2013.01); *A61M 5/3155* (2013.01);
(Continued)

(58) Field of Classification Search
CPC ........ A61M 5/3137; A61M 2005/3139; A61M 2205/586
See application file for complete search history.

(56) References Cited

U.S. PATENT DOCUMENTS

| 533,575 A | 2/1895 | Wilkens |
| 5,226,895 A | 7/1993 | Harris |

(Continued)

FOREIGN PATENT DOCUMENTS

| CN | 1399567 A | 2/2003 |
| CN | 102413856 A | 4/2012 |

(Continued)

OTHER PUBLICATIONS

International Search Report for Int. App. No. PCT/EP2014/054533, completed May 5, 2014.
(Continued)

*Primary Examiner* — Kami A Bosworth
*Assistant Examiner* — William Carpenter
(74) *Attorney, Agent, or Firm* — McDonnell Boehnen Hulbert & Berghoff LLP

(57) ABSTRACT

The present disclosure concerns an attachment for an operable drug delivery device, comprising a gripping sleeve member that is configured to receive a first member of the operable drug delivery device, wherein the gripping sleeve member comprises a first gripping sleeve member part comprising a first engagement feature at its inner surface that is configured to engage the first gripping sleeve member part in a torque-proof manner with the first member of the operable drug delivery device. Further, the present invention
(Continued)

concerns a use of the attachment or a system of attachments for operating the operable drug delivery device.

16 Claims, 19 Drawing Sheets

(52) U.S. Cl.
CPC ............... *A61M 2005/3139* (2013.01); *A61M 2205/586* (2013.01)

(56) References Cited

U.S. PATENT DOCUMENTS

| | | | |
|---|---|---|---|
| 5,279,586 A | | 1/1994 | Balkwill |
| 5,304,152 A | | 4/1994 | Sams |
| 5,320,609 A | | 6/1994 | Haber et al. |
| 5,383,865 A | * | 1/1995 | Michel ............... A61M 5/31553 604/186 |
| 5,480,387 A | | 1/1996 | Gabriel et al. |
| 5,505,704 A | | 4/1996 | Pawelka et al. |
| 5,582,598 A | | 12/1996 | Chanoch |
| 5,626,566 A | | 5/1997 | Petersen et al. |
| 5,674,204 A | | 10/1997 | Chanoch |
| 5,688,251 A | | 11/1997 | Chanoch |
| 5,921,966 A | * | 7/1999 | Bendek ............... A61M 5/24 604/207 |
| 5,957,896 A | | 9/1999 | Bendek et al. |
| 5,961,495 A | | 10/1999 | Walters et al. |
| 6,004,297 A | | 12/1999 | Steenfeldt-Jensen et al. |
| 6,193,698 B1 | | 2/2001 | Kirchhofer et al. |
| 6,221,046 B1 | | 4/2001 | Burroughs et al. |
| 6,235,004 B1 | | 5/2001 | Steenfeldt-Jensen et al. |
| 6,248,095 B1 | | 6/2001 | Giambattista et al. |
| 6,277,099 B1 | * | 8/2001 | Strowe ............... A61M 5/31553 604/186 |
| 6,287,283 B1 | | 9/2001 | Ljunggreen et al. |
| 6,899,698 B2 | | 5/2005 | Sams |
| 6,936,032 B1 | | 8/2005 | Bush, Jr. et al. |
| 7,241,278 B2 | | 7/2007 | Moller |
| 9,289,551 B2 | * | 3/2016 | Hata ............... A61M 5/20 |
| 2002/0052578 A1 | | 5/2002 | Moller |
| 2002/0120235 A1 | | 8/2002 | Enggaard |
| 2003/0050609 A1 | * | 3/2003 | Sams ............... A61M 5/20 604/208 |
| 2004/0059299 A1 | | 3/2004 | Moller |
| 2004/0210199 A1 | | 10/2004 | Atterbury et al. |
| 2004/0267207 A1 | | 12/2004 | Veasey et al. |
| 2005/0113765 A1 | | 5/2005 | Veasey et al. |
| 2006/0153693 A1 | | 7/2006 | Fiechter et al. |
| 2008/0125723 A1 | * | 5/2008 | Leiner ............... A61O 5/62 604/211 |
| 2008/0306434 A1 | * | 12/2008 | Dobbles ............... A61B 5/0002 604/66 |
| 2009/0275916 A1 | | 11/2009 | Harms et al. |
| 2011/0257604 A1 | * | 10/2011 | Banik ............... A61M 5/484 604/209 |
| 2011/0313350 A1 | * | 12/2011 | Krulevitch ............... A61M 5/24 604/65 |

FOREIGN PATENT DOCUMENTS

| | | |
|---|---|---|
| EP | 0937471 | 8/1999 |
| EP | 0937476 | 8/1999 |
| WO | 99/38554 | 8/1999 |
| WO | 01/10484 | 2/2001 |
| WO | 01/13977 A1 | 3/2001 |
| WO | 2010/098927 | 9/2010 |
| WO | 2010/098928 A1 | 9/2010 |
| WO | 2011/057677 | 5/2011 |
| WO | 2012/000832 | 1/2012 |
| WO | 2012/000832 A1 | 1/2012 |

OTHER PUBLICATIONS

Chinese Office Action for CN Application No. 201480011785.0, dated Jul. 14, 2017.

Chinese Office Search Report for CN Application No. 201480011785.0, dated Jul. 5, 2017.

* cited by examiner

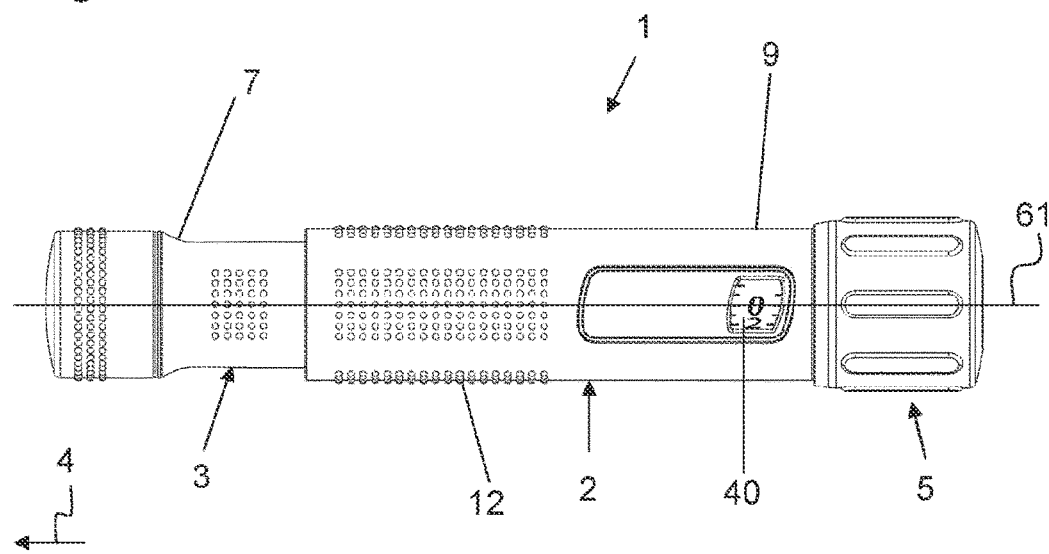
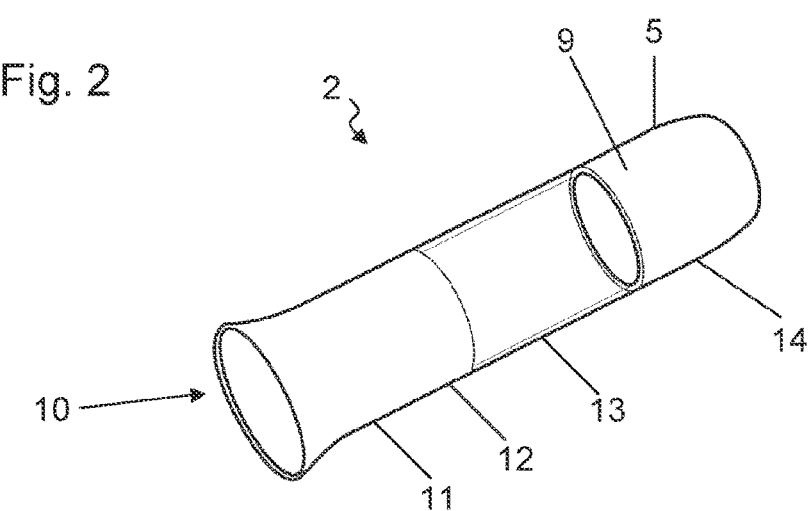

ADD-ON GRIP AND ACTUATION-SLEEVE FOR A PEN-TYPE DRUG INJECTION DEVICE

CROSS REFERENCE TO RELATED APPLICATIONS

The present application is a U.S. National Phase Application pursuant to 35 U.S.C. § 371 of International Application No. PCT/EP2014/054533 filed Mar. 10, 2014, which claims priority to European Patent Application No. 13159056.4 filed Mar. 13, 2013. The entire disclosure contents of these applications are herewith incorporated by reference into the present application.

TECHNICAL FIELD

The present invention relates to an attachment for an operable drug delivery device. Further, the present invention relates to a use of the attachment or a system of attachments for operating the operable drug delivery device.

BACKGROUND

Drug delivery devices are generally known for the administration of a medicinal product, for example insulin or heparin, but also for other medicinal products, in particular for self-administration by a patient.

Patients with impaired dexterity can experience difficulties in selecting or administering a dose of a medicinal product using a standard operable drug delivery device. Due to the size of the dose dial member and/or the gripping features, people with impaired motor functions or people with severe arthritis can be unable to dial a dose. To dispense a dose in a standard operable drug delivery device, the patient has to extend his thumb to press a dial. For users with impaired finger dexterity reaching the dial can be difficult whilst holding the drug delivery device safely. Further, the patients may be unable to produce enough force to dispense the dose when their thumb is extended. These cases can lead to misuse of an operable drug delivery device and cause potential risk for the patient, e.g. by an over- or under-dose or by injury during a dose setting or dose dispense operation.

SUMMARY

It is an object of the present disclosure to provide an ergonomic solution for operating a drug delivery device.

This object is solved by the attachment according to present claim 1. Further, this object is solved by the use of the attachment or the system of attachments according to the further independent claim.

According to a first aspect of the present disclosure, an attachment for an operable drug delivery device is provided comprising a gripping sleeve member that is configured to receive a first member of the operable drug delivery device wherein the gripping sleeve member comprises a first gripping sleeve member part comprising a first engagement feature at its inner surface that is configured to engage the first gripping sleeve member part in a torque-proof manner with the first member of the operable drug delivery device.

The operable drug delivery device is fully operable without the attachment. In particular, the operable drug delivery device is configured to carry out a dose setting and a dose dispense operation if the attachment is not attached to the operable drug delivery device. The operable drug delivery device may comprise a medicinal product. A dose setting operation may be an operation which determines the amount of the medicinal product which is dispensed in the next dose dispense operation. A dose dispense operation may be an operation of dispensing the medicinal product.

The attachment for the operable drug delivery device may be added to the operable drug delivery device either during assembly or later by a user as an add-on attachment. The attachment is configured to be attached to the first member of the operable drug delivery device wherein the first member may be an outer member of the operable drug delivery device. An outer member is defined as a member forming at least a part of the outer surface of the operable drug delivery device. The first member may be a dose dial member, a housing or a cartridge holder.

The gripping sleeve member is configured to receive the first member of the operable drug delivery device. In particular, the gripping sleeve member may be configured to cover at least 10% of the operable drug delivery device when the attachment is attached to the operable drug delivery device. Preferably, the gripping sleeve member covers at least 40% of the operable drug delivery device when the attachment is attached to the operable drug delivery device. The gripping sleeve member may be dimensioned such that it can be easily held in a full hand grip. Accordingly, the gripping sleeve member may have a length in the longitudinal direction of at least 5 cm. The gripping sleeve member may have a length in the longitudinal direction in the range of 5 to 20 cm, preferably of 8 to 16 cm.

As the gripping sleeve member may be engaged with the first member of the operable drug delivery device in a torque-proof manner, a user with limited dexterity is able to operate the operable drug delivery device. The gripping sleeve member may provide a large surface that is easy to grip. Further, the gripping sleeve member may provide a larger handle compared to the first member. Thus, the patient has to apply a smaller torque to rotate the first member. Accordingly, the attachment improves the torsional mechanical advantage. Thus, operating the operable drug delivery device via the gripping sleeve member provides an improved ergonomic solution as it allows comfortably operating the operable drug delivery device even for patients with impaired dexterity.

The term "to receive a member" is defined as follows. When the first member is received in the gripping sleeve member, the gripping sleeve member covers at least a part of the first member. In particular, the gripping sleeve member may surround the first member of the operable drug delivery device.

The first engagement feature is configured to engage the first gripping sleeve member part in a torque-proof manner with the first member. A torque-proof manner means that a rotation of the first gripping sleeve member part is transferred to a rotation of the first member by the same rotary angle.

The gripping sleeve member may comprise the first gripping sleeve member part and other parts. Alternatively, the gripping sleeve member may consist of only the first gripping sleeve member part. The first gripping sleeve member part may be engaged to the first member in a way that the engagement can only be released if one of the first gripping sleeve member part or the first member is damaged. In an alternate embodiment, the first gripping sleeve member part may be releasably engaged with the first member such that the engagement can be released without damaging one of the first gripping sleeve member part or the first member.

The first engagement feature may be a protrusion. The first engagement feature may be configured to engage the first gripping sleeve member part in a snap-fit connection.

The operable drug delivery device may be an injection device. In particular, the operable drug delivery device may be a pen-type injection device. Moreover, the operable drug delivery device may be configured to dispense variable, preferably user-settable, doses of the drug. Alternatively, the operable drug delivery device may also be a fixed dose device, in particular a device configured to dispense doses of the drug which may not be varied by the user. The operable drug delivery device may be a disposable or a re-usable device. The operable drug delivery device may be a manually, in particular a non-electrically, driven device.

As already discussed above, the operable drug delivery device is fully operable without the attachment. In particular, the operable drug delivery device may comprise a drive mechanism. The drive mechanism may comprise a piston rod. The piston rod may comprise a bearing that is configured to exert a force on a bung of a cartridge in a distal direction to expel a medicinal product form the cartridge.

The terms "distal" and "proximal" shall be defined as follows. The distal end of the operable drug delivery device is defined as the end which is closest to a dispensing end of the drug delivery device. The proximal end of the operable drug delivery device is defined as the end which is furthest away from the dispensing end of the drug delivery device. Moreover, a distal direction is defined as a direction towards the distal end and a proximal direction is defined as a direction towards the proximal end.

The drive mechanism of the operable drug delivery device may further comprise a drive member and a dose dial member. The drive member may be a drive sleeve. The dose dial member may be a button. A user may have to move the dose dial member to set a dose and/or to dispense a dose. The movement of the dose dial member may be transferred to a movement of the drive sleeve. Further, the drive sleeve may be configured to move the piston rod.

Moreover, the operable drug delivery device may comprise a cartridge holder comprising the cartridge which contains the medicinal product and the bung. Further, the operable drug delivery device may comprise an inner body and/or a housing. The operable drug delivery device may further comprise a window in the housing. A number corresponding to the state of the operable drug delivery device may be visible in the window. The number may e.g. correspond to the currently set number of doses.

The first engagement feature may be configured to transfer a movement of the first gripping sleeve member part to a movement of the first member of the operable drug delivery device. In particular, if the attachment is engaged with the operable drug delivery device, a patient may move the first gripping sleeve member part during a dose setting and/or a dose dispense operation, thereby moving the first member as the movement of the first gripping sleeve member part is transferred to a movement of the first member. The first engagement feature may engage the first gripping sleeve member part with the first member such that it is not possible to move the first gripping sleeve member part relative to the first member when the engagement feature is engaged.

The attachment may comprise a torque limiting mechanism defining a maximum allowed torque, wherein the first gripping sleeve member part may be coupled with the first member of the operable drug delivery device via the torque limiting mechanism which is configured to prevent a movement of the first gripping sleeve member part being transferred to a movement of the first member if a torque is applied to the first gripping sleeve member part which is greater than the maximum allowed torque. Accordingly, the torque limiting mechanism may prevent that the first member of the operable drug delivery device is damaged by an excessive torque applied to the first gripping sleeve member part.

The operable drug delivery device may comprise a rotational end stop feature wherein the first member abuts the rotational end stop feature if a maximum number of doses is set. If a patient tries to further rotate the first gripping sleeve member part, the torque applied to the first gripping sleeve member part is further increased. Without the torque limiting mechanism, this may result in damaging either the first member or the rotational end stop feature. However, the torque limiting mechanism prevents a torque being greater than the maximum allowed torque to be applied to the first member such that this damage is prevented.

The torque limiting mechanism may comprise a clutch member configured to slip when a torque greater than the maximum allowed torque is applied to the first gripping sleeve member part. The clutch member may be engageable with the gripping sleeve member. In particular, a torque applied to the first gripping sleeve member part may be transferred to a torque applied to the clutch member. Further, the clutch member may engage with engagement features of the first member. If a torque smaller than the maximum allowed torque is applied to the clutch member being engaged with the first member, the clutch member forms a torque-proof connection with the first member such that the first member follows a rotation of the gripping sleeve member. Further, if a torque greater than the maximum allowed torque is applied to the clutch member, the clutch member may disengage the first member from the gripping sleeve member such that the first member does not follow a rotation of the gripping sleeve member.

The gripping sleeve member may comprise an opening for receiving the first member of the operable drug delivery device, wherein the first engagement features may be arranged at an end of the gripping sleeve member opposite to the opening. To engage the first member with the first gripping sleeve member part, the operable drug delivery device has to be moved into the opening.

The first engagement feature may be configured to engage the first gripping sleeve member part releasably with the first member of the operable drug delivery device. A releasable engagement may be defined such that the first gripping sleeve member part can be removed from the first member without damaging either one of the first gripping sleeve member part or the first member.

The gripping sleeve member may comprise a first disengagement feature being movable between a first and a second position wherein the first disengagement feature is configured not to disengage the gripping sleeve member from the first member of the operable drug delivery device in its first position and wherein the first disengagement feature is configured to disengage the gripping sleeve member from the first member of the operable drug delivery device in its second position. The first disengagement feature may be configured such that the attachment can be separated from the drug delivery device without damaging either one of the attachment or the drug delivery device.

The first disengagement feature may comprise a tapered surface. The tapered surface may be arranged in an angle ranging from 10° to 80° to a longitudinal axis of the operable drug delivery device when the attachment is attached to the operable drug delivery device. As the disengagement feature may allow disengagement of the attachment from the operable drug delivery device, the attachment may be reused with different operable drug delivery devices. In particular, the operable drug delivery device may be a disposable device. In this case, the user may simply remove the attachment after the last dose has been delivered and the device is considered empty and, afterwards, the user may reattach the attachment to another operable drug delivery device.

Further, the attachment may comprise a spring member providing a spring force tending to move the first gripping sleeve member part into engagement with the first member of the operable drug delivery device.

The spring member may tend to move the first disengagement feature into its first position. Accordingly, the spring force has to be overcome to disengage the attachment from the operable drug delivery device. Thereby, the spring member may prevent an accidental disengagement of the attachment from the operable drug delivery device.

Further, the spring member may be configured to cooperate with the torque limiting mechanism. In particular, the spring member may apply a force onto the clutch member which tends to engage the clutch member with the engagement feature of the first member. Accordingly, if the clutch member has been disengaged from the first member, e.g. due to the application of an excessive torque greater than the maximum allowed torque, the spring member may ensure that the clutch member is later reengaged with the first member.

Further, the gripping sleeve member may comprise a second gripping sleeve member part which may be permitted to rotate relative to the first gripping sleeve member part and which may be prevented from moving axially relative to the first gripping sleeve member part. In particular, the second gripping sleeve member part may be axially secured, but rotatable with respect to the first gripping sleeve member part.

In particular, the engagement features of the gripping sleeve member may be part of the first gripping sleeve member part. When the gripping sleeve member is attached to the operable drug delivery device, the second gripping sleeve member part may be prevented from rotating relative to the housing of the operable drug delivery device.

The second gripping sleeve member part may comprise a disengagement feature, wherein the disengagement feature is configured to disengage the releasable engagement of the first gripping sleeve member part with the first member when the first gripping sleeve member part is moved relative to the second gripping sleeve member part. In particular, said relative movement may be an axial movement wherein the first and the second gripping sleeve member parts are moved towards each other.

In particular, the disengagement feature of the second gripping sleeve member part may be a second disengagement feature, wherein the second gripping sleeve member part may be configured such that a movement of the first gripping sleeve member relative to the second gripping sleeve member part engages the second disengagement feature with the first disengagement feature, thereby moving the first disengagement feature into its first position. The engagement of the first and the second disengagement feature may be an abutment.

A further aspect of the present disclosure concerns a system of attachments for an operable drug delivery device which comprises an attachment and further a guarding sleeve member that is configured to be attached to the operable drug delivery device and to receive a second member of the operable drug delivery device.

In particular, the attachment may be the attachment disclosed above such that every structural and functional feature disclosed with respect to that attachment may also be present in the system of attachments.

The second member of the operable drug delivery device may be an outer member. For example, the second member may be a cartridge holder or a part of the housing of the operable drug delivery device.

The guarding sleeve member may provide protection for a needle attached to the distal end of the drug delivery device. Further, when attached to the second member of the drug delivery device, the guarding sleeve member may project in the distal direction beyond the distal end of the operable drug delivery device. Accordingly, the guarding sleeve member may define a distal contact surface of a kit comprising the operable drug delivery device and the system of attachments. The distal contact surface may provide improved stability when abutting a surface, e.g. the skin of the user.

The guarding sleeve member may comprise a first orientation member and the second gripping sleeve member part may comprise a second orientation member, wherein the first and the second orientation member are configured to be engageable with each other only when the guarding sleeve member and the second gripping sleeve member part are oriented relative to each other in a predetermined relative rotational position. Each of the first and the second orientation member may comprise at least one of a protrusion or a slot. Due to an engagement of the first and the second orientation members, the guarding sleeve member and the second gripping sleeve member part are prevented from rotating relative to each other when attached to an operable drug delivery device during a dose setting or a dose dispense operation of the operable drug delivery device.

Further, the system may comprise a cap member which is engageable with the guarding sleeve member and which is configured to close an opening of the guarding sleeve member when engaged with the guarding sleeve member. The cap member, the guarding sleeve member and the gripping sleeve member may form a cavity for receiving the operable drug delivery device.

The cap member may comprise curved edge features which provide an easy grip of the cap member, thereby ensuring that the cap member can be easily attached to or removed from the guarding sleeve member. Therefore, the cap member can be attached or removed by persons with impaired finger dexterity.

The gripping sleeve member may be configured to at least partly receive the guarding sleeve member. Accordingly, an opening defined in the gripping sleeve member has a radius which is greater than the radius of the guarding sleeve member.

Another aspect of the present disclosure concerns a kit comprising an attachment for an operable drug delivery device or a system of attachments for the operable drug delivery device and the operable drug delivery device comprising a first and a second member.

In particular, the attachment and the system of attachments may be the attachment and the system discussed above such that every structural and functional feature disclosed with respect to either the attachment or the system of attachments may also be present in the kit. Further, the operable drug delivery device may be the operable drug delivery device discussed above such that every structural and functional feature disclosed with respect to the operable drug delivery device may also be present in the kit.

The first member may comprise a dose dial member which is configured to be rotated relative to the second member of the operable drug delivery device for a dose setting operation and/or for a dose dispense operation of the operable drug delivery device. The first member may also be configured to be moved axially relative to the second member of the operable drug delivery device.

Further, a radius of the gripping sleeve member may be greater than a radius of the first member of the operable drug delivery device.

Further, the first member may comprise a second engagement feature and the second engagement feature and the first engagement feature of the gripping sleeve member are configured to be connected with each other by a snap-fit connection. In particular, the second engagement feature of the first member may be a recess. The second engagement feature of the first member may also be configured to be engaged with the clutch member.

Another aspect of the present disclosure concerns the use of an attachment or a system of attachments for operating an operable drug delivery device.

In this aspect, the attachment, the system of attachments and the operable drug delivery device may be the attachment, the system of attachments and the operable drug delivery device disclosed above such that every structural and functional feature disclosed with respect to the attachment, the system and the device may also be present here.

Another aspect of the present disclosure concerns a method of operating an operable drug delivery device using an attachment or a system of attachments. In this aspect, the attachment, the system of attachments and the operable drug delivery device may be the attachment, the system of attachments and the operable drug delivery device disclosed above such that every structural and functional feature disclosed with respect to the attachment, the system and the device may also be present with respect to the method.

The method may comprise the steps of:
attaching the first attachment to the operable drug delivery device by engaging the first engaging means with the first member, and
operating the operable drug delivery device by using the first attachment.

Further, the method may comprise the step of attaching the system of attachments and operating the operable drug delivery device by using said system. The step of operating the drug delivery device may comprise the sub-steps of performing a dose setting operation and/or a dose dispense operation.

The term "medicinal product", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2, H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

In the following, the disclosed invention is described in further detail with reference to the drawings, wherein

BRIEF DESCRIPTION OF THE FIGURES

FIG. 1 shows a kit comprising an operable drug delivery device, a first attachment and a second attachment.

FIG. 2 shows a perspective view of the first attachment shown in FIG. 1.

DETAILED DESCRIPTION

Figure 3:
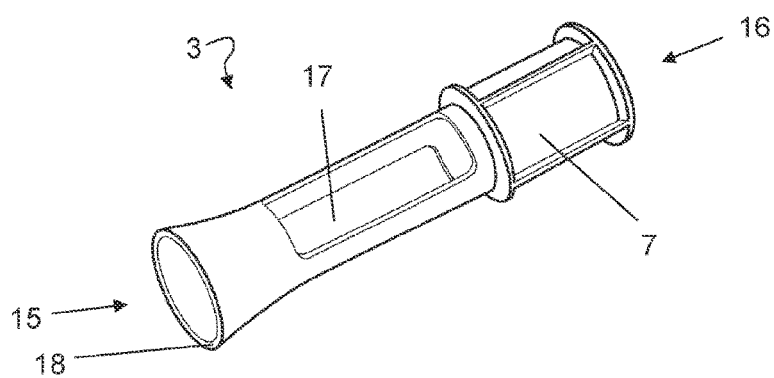
FIG. 3 shows a perspective view of the second attachment shown in FIG. 1.

FIG. 1 shows a kit comprising an operable drug delivery device 1, a first attachment 2 and a second attachment 3. The first and the second attachment 2, 3 are attached to the operable drug delivery device 1.

The operable drug delivery device 1 shown in FIG. 1 is a pen-type injection device configured to allow setting of variable doses.

The operable drug delivery device 1 is fully operable without the first or the second attachment 2, 3. In particular, the operable drug delivery device 1 comprises a drive mechanism (not shown) which may be configured to move a piston rod in a distal direction 4. The drive mechanism of the operable drug delivery device may further comprise a drive member and a dose dial member. The drive member may be a drive sleeve. The dose dial member may be a button. A user may have to move the dose dial member to set a dose and/or to dispense a dose. The movement of the dose dial member may be transferred to a movement of the drive sleeve. Further, the drive sleeve may be configured to move a piston rod.

Moreover, the operable drug delivery device 1 may comprise a cartridge holder (not shown) comprising the cartridge which comprises the medicinal product and the bung. Further, the operable drug delivery device 1 may comprise an inner body and/or a housing. The operable drug delivery device 1 may further comprise a window 40 in the housing. A number corresponding to the state of the operable drug delivery device 1 may be visible in the window 40. The number may e.g. correspond to the currently set number of doses.

The first attachment 2 comprises a gripping sleeve member 5. The gripping sleeve member 5 is configured to receive a first member 6 (not shown in FIG. 1) of the operable drug delivery device 1. In the embodiment shown in FIG. 1, the first member 6 received by the gripping sleeve member 5 is the dose dial member of the operable drug delivery device 1.

Further, the second attachment 3 comprises a guarding sleeve member 7 which is configured to receive a second member 8 (not shown in FIG. 1) of the operable drug delivery device 1. In the embodiment shown in FIG. 1, the second member 8 of the operable drug delivery device 1 received by the guarding sleeve member 7 is the cartridge holder. In alternative embodiments, a part of the housing of the operable drug delivery device 1 may be the second member 8 received by the guarding sleeve member 7.

In an alternate embodiment, the kit may comprise the operable drug delivery device 1 and only one of the first and the second attachment 2, 3. Each of the first and the second attachment 2, 3 may be attached to the operable drug delivery device 1 independently of the respective other attachment 2, 3.

FIG. 2 shows the first attachment 2 comprising the gripping sleeve member 5 according to a first embodiment. In the first embodiment the gripping sleeve member 5 consists of a first gripping sleeve member part 9.

The gripping sleeve member 5 comprises an opening 10 for receiving the first member 6 of the operable drug delivery device 1. The opening 10 is arranged at one end of the gripping sleeve member 5. The gripping sleeve member 5 is closed at the end opposite of the opening 10. When the gripping sleeve member 5 is attached to the operable drug delivery device 1, the proximal end of the operable drug delivery device 1 is entered through the opening 10.

The first gripping sleeve member part 9 comprises a first part 11 comprising the opening 10 and stretching over roughly a third of the length of the first gripping sleeve member part 9. The first part 11 is a gripping part. The first part 11 comprises a structured surface 12 providing an increased friction and, thus, allowing for an easy grip of a patient. In the embodiment shown in FIG. 1, the structured surface 12 of the first part 9 comprises dot-shaped protrusions.

Further, the first gripping sleeve member part 9 comprises a part 13 that is at least partially transparent. The at least partially transparent part 13 is adjacent to the first part 11 in a direction away from the opening 10. When the first gripping sleeve member part 9 is attached to the operable drug delivery device 1, the at least partially transparent part 13 of the first gripping sleeve member part 9 overlaps with the window 40 in the housing of the operable drug delivery device 1. Accordingly, the number shown in the window is visible when the gripping sleeve member 5 is attached to the operable drug delivery device 1.

The first gripping sleeve member part 9 comprises a last part 14 which is adjacent to the at least partially transparent part 13 in a direction away from the opening 10. The last part 14 comprises the closed end.

The radius of the gripping sleeve member 5 is greatest in the first part 11 near the opening 10 of the gripping sleeve member 5. In a sub-part of the first part 11 arranged at a distance from the opening 10 and in the other parts 13, 14 of the first gripping sleeve member part 9 the radius is constant.

The gripping sleeve member 5 has a radius that is greater than the radius of the operable drug delivery device 1. In particular, the radius of the opening 10 of the gripping sleeve member 5 is greater than the radius of the operable drug delivery device 1 taken any point along a longitudinal axis 61 of the operable drug delivery device 1. Accordingly, the gripping sleeve member 5 is configured to at least partially receive the operable drug delivery device 1.

FIG. 3 shows the second attachment 3 comprising the guarding sleeve member 7. The guarding sleeve member 7 comprises a first opening 15 at one end and a second opening 16 at the opposite end. The first and the second opening 15, 16 are connected by a channel formed through the guarding sleeve member 7. Further, a window 17 is defined in the guarding sleeve member 7. When the guarding sleeve member 7 is attached to the operable drug delivery device 1, the window 17 of the guarding sleeve member 7 overlaps the window 40 in the housing of the operable drug delivery device 1. Further, when the guarding sleeve member 7 and the gripping sleeve member 5 are concurrently attached to the operable drug delivery device 1, the at least partially transparent part 13 of the first gripping sleeve member part 9 overlaps the window 17 of the guarding sleeve member 7.

Further, the guarding sleeve member 7 comprises a contact surface 18 arranged at the first opening 15 of the guarding sleeve member 7. The contact surface 18 is circular shaped. When the guarding sleeve member 7 is attached to the operable drug delivery device 1 and a dose dispense operation is carried out, the contact surface 18 of the guarding sleeve member 7 may abut the skin of the patient. The contact surface 18 of the guarding sleeve member 7 is bigger than the surface of the operable drug delivery device 1 that contacts the skin of the patient if the dose dispense operation is carried out with the operable drug delivery device 1 and without the guarding sleeve member 7. Thereby, the contact surface 18 provides a more stable connection to the skin of the patient, thus increasing the usability of the kit and allowing a person with impaired finger dexterity to carry out the dose dispense operation.

The guarding sleeve member 7 has a radius that is greater than the radius of the operable drug delivery device 1. In particular, the radius of the channel through the guarding sleeve member 7 is greater than the radius of the operable drug delivery device 1 taken any point along the longitudinal axis 61 of the operable drug delivery device 1. Accordingly, the guarding sleeve member 7 is configured to at least partially receive the operable drug delivery device 1.

Moreover, the radius of the gripping sleeve member 5 is greater than the radius of the guarding sleeve member 7. Accordingly, the gripping sleeve member 5 is configured to at least partially receive the guarding sleeve member 7. In particular, when both attachments 2, 3 are attached to the operable drug delivery device 1, the gripping sleeve member 5 partly receives the guarding sleeve member 7.

Figure 4:
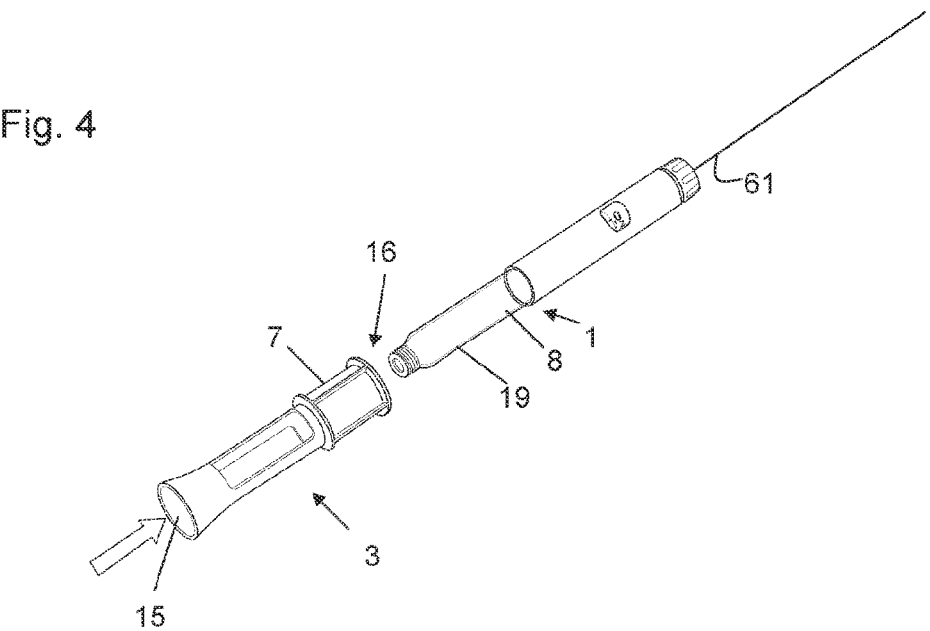
FIG. 4 shows a kit comprising an operable drug delivery device and a second attachment comprising a guarding sleeve member wherein the guarding sleeve member is not attached to the operable drug delivery device.

FIG. 4 shows a kit comprising the operable drug delivery device 1 and the second attachment 3 comprising the guarding sleeve member 7. In FIG. 4, the guarding sleeve member 7 is not attached to the operable drug delivery device 1. To attach the guarding sleeve member 7 to the operable drug delivery device 1, the distal end of the operable drug delivery device 1 is entered through the second opening 16 of the guarding sleeve member 7, as indicated in FIG. 4.

Figure 5:
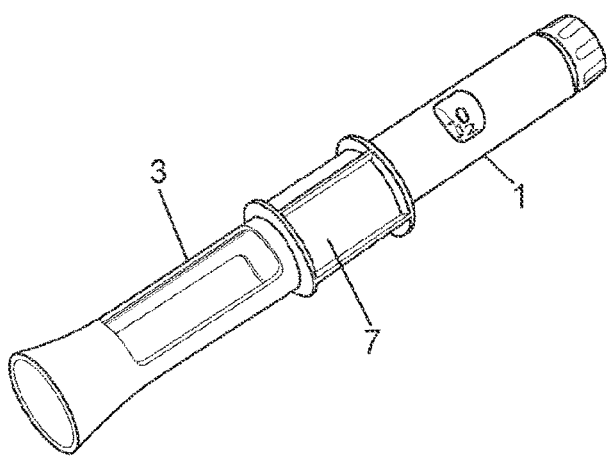
FIG. 5 shows the kit shown in FIG. 4 wherein the guarding sleeve member is attached to the operable drug delivery device.

FIG. 5 shows the kit comprising the guarding sleeve member 7 and the operable drug delivery device 1 wherein the guarding sleeve member 7 is attached to the operable drug delivery device 1. The guarding sleeve member 7 receives a second member 8 of the operable drug delivery device 1. In this embodiment, the second member 8 is the cartridge holder 19.

When the guarding sleeve member 7 is attached to the operable drug delivery device 1, the guarding sleeve member 7 projects beyond the end of the operable drug delivery device 1 in the distal direction 4.

Figure 6:
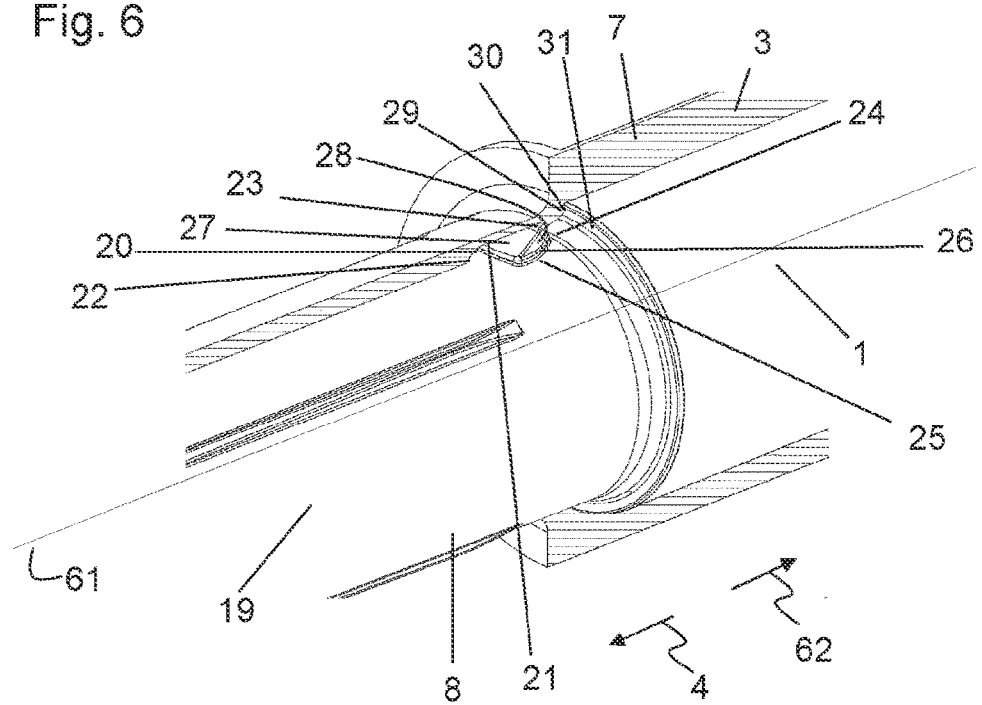
FIG. 6 shows a more detailed view of the engagement of the guarding sleeve member with a second member of the operable drug delivery device.

FIG. 6 shows a more detailed view of the engagement of the guarding sleeve member 7 with the second member 8 of the operable drug delivery device 1. In FIG. 6, the guarding sleeve member 7 is shown in a cross-sectional view.

The guarding sleeve member 7 comprises an engagement feature 20 at its inner surface. The engagement feature 20 of the guarding sleeve member 7 comprises an indentation 21. The indentation 21 extends in a direction from the first opening 15 towards the second opening 16 of the guarding sleeve member 7. In particular, the indentation 21 is formed by a first wall 22 facing towards the first opening 15 and a second wall 23 facing towards the second opening 16. The first wall 22 defining the indentation 21 is formed as a smooth curve. The second wall 23 defining the indentation 21 is arranged at an angle in the range of 70° to 130° to the end of the first wall 22, thereby forming a sharp edge. The engagement feature 20 of the guarding sleeve member 7 defines a pull out end stop feature 24. In particular, the second wall 23 formed as a sharp edge defines the pull out end stop feature 24. The pull out end stop feature 24 prevents an axial movement of the guarding sleeve member 7 relative to the second member 8 in the distal direction 4 when the guarding sleeve member 7 is engaged with the second member 8.

Further, the second member 8 of the operable drug delivery device 1 comprises a corresponding engagement feature 25. The engagement feature 25 of the second member 8 comprises a protrusion 26. The engagement feature 25 of the second member 8 has a distal face 27 and a proximal face 28. The distal face 27 of the engagement feature 25 of the second member 8 is arranged at a smooth angle relative to the longitudinal axis 61 of the operable drug delivery device 1 in the range of 5° to 60°. Accordingly, the distal face 27 of the engagement feature 25 of the second member 8 is formed such that the guarding sleeve member 7 is allowed to slide over the engagement feature 25 of the second member 8 in a proximal direction 62. Further, the proximal face 28 of the engagement feature 25 of the second member 8 is tapered relative to the longitudinal axis 61 of the operable drug delivery device 1 in a steep angle, e.g. an angle in the range of 80° to 150°. Accordingly, the proximal face 28 of the engagement feature 25 of the second member 8 is formed such that the guarding sleeve member 7 is prevented from sliding over the engagement feature 25 of the second member 8 in the distal direction 4 once the engagement features 20, 25 of the guarding sleeve member 7 and of the second member 8 are engaged with each other.

The engagement features 20, 25 of the guarding sleeve member 7 and of the second member 8 are configured to be engaged with each other by a snap-fit connection. When engagement features 20, 25 of the guarding sleeve member 7 and of the second member 8 are engaged with each other, the guarding sleeve member 7 is prevented from rotating or moving axially relative to the second member 8 of the operable drug delivery device 1.

As discussed above, when the guarding sleeve member 7 is engaged with the second member 8, an axial movement of the guarding sleeve member 7 relative to the second member 8 in the distal direction 4 is prevented by an abutment of the proximal face 28 of the engagement feature 25 of the second member 8 and the pull out end stop feature 24 defined by the engagement feature 20 of the guarding sleeve member 7.

Moreover, the guarding sleeve member 7 comprises a push in end stop feature 29 which limits the distance by which the second member 8 of the operable drug delivery device 1 can be moved relative to the guarding sleeve member 7 in the distal direction 4. The push in end stop feature 29 comprises an abutment surface 30. The second member comprises a corresponding abutment surface 31. When the second member 8 has been moved relative to the guarding sleeve member 7 by the maximum allowed distance in the distal direction 4, the push in end stop feature 29 of the guarding sleeve member 7 abuts the abutment surface 31 of the second member 8, thereby preventing further axial movement of the guarding sleeve member 7 relative to the second member 8 in the proximal direction.

The guarding sleeve member 7 is dimensioned such that the push in end stop feature 29 abuts the abutment surface 31 of the second member 8 in the relative position in which the engagement features 20, 25 of the guarding sleeve member 7 and the second member 8 are engaged with each other. Thus, the guarding sleeve member 7 is prevented from moving axially relative to the second member 8 of the operable drug delivery device 1 in this position.

Further, the engagement features 20, 25 of the guarding sleeve member 7 and of the second member 8 are configured such that a rotational movement of the guarding sleeve member 7 relative to the second member 8 is prevented when the engagement features 20, 25 are engaged with each other. In particular, the engagement features 20, 25 are not rotary symmetric.

Figure 7:
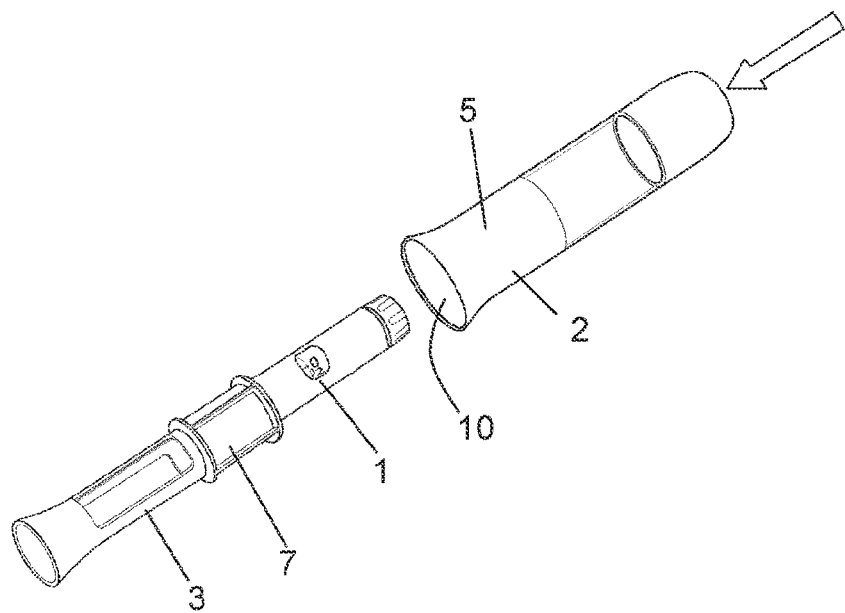
FIG. 7 shows the kit shown in FIGS. 4 to 6 and a first attachment comprising a gripping sleeve member wherein the gripping sleeve member is not attached to the operable drug delivery device.

FIG. 7 shows the kit comprising the operable drug delivery device 1, the first attachment 2 comprising the gripping sleeve member 5 and the second attachment 3 comprising the guarding sleeve member 7. In FIG. 7, the guarding sleeve member 7 is engaged with the second member 8 of the operable drug delivery device 1. The gripping sleeve member 5 is not attached to the operable drug delivery device 1. To attach the gripping sleeve member 5 to the operable drug delivery device 1, the operable drug delivery device 1 is inserted into the opening 10 of the gripping sleeve member 5.

Figure 8:
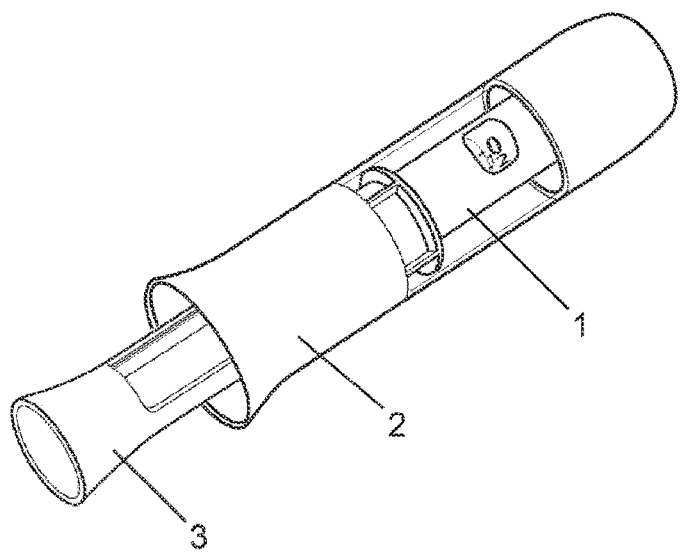
FIG. 8 shows the kit shown in FIG. 7 wherein the gripping sleeve member is attached to the operable drug delivery device.

FIG. 8 shows the gripping sleeve member 5 being attached to the operable drug delivery device 1.

Figure 9:
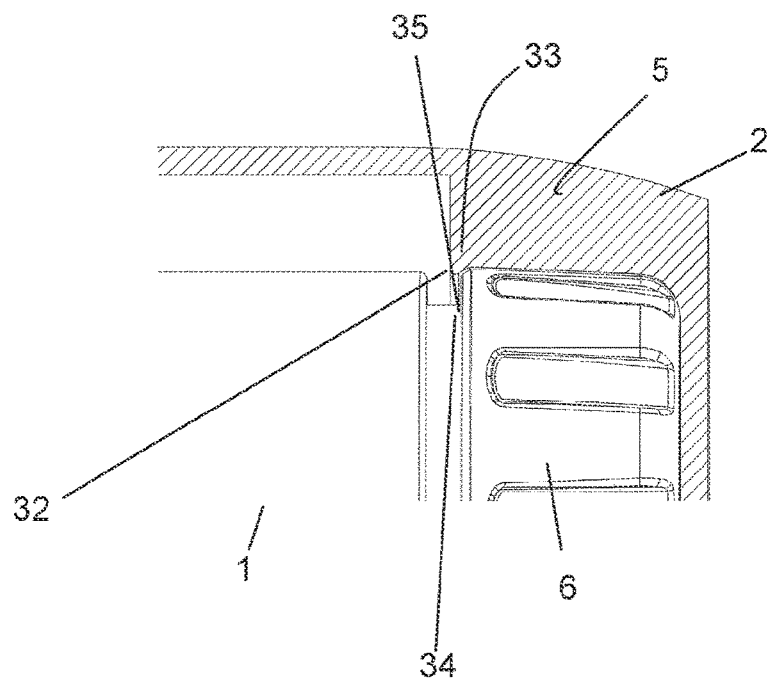
FIG. 9 shows a cross-sectional view of the engagement of the gripping sleeve member with a first member of the operable drug delivery device of FIGS. 7 and 8.

FIG. 9 shows a detailed cross-sectional view of the gripping sleeve member 5 being attached to the operable drug delivery device 1. The gripping sleeve member 5 comprises an engagement feature 32. The engagement feature 32 of the gripping sleeve member 5 is arranged at an inner surface of the gripping sleeve member 5. The engagement feature 32 of the gripping sleeve member 5 is arranged at an end opposite to the opening 10 of the gripping sleeve member 5. The engagement feature 32 of the gripping sleeve member 5 comprises a projecting element 33.

The first member 6 of the operable drug delivery device 1 comprises an engagement feature 34. The engagement feature 32 of the gripping sleeve member 5 is configured to be engaged with the engagement feature 34 of the first member 6. The engagement feature 34 of the first member 6 comprises a recess 35. When the engagement features 32, 34 of the gripping sleeve member 5 and of the first member 6 are engaged with each other, the gripping sleeve member 5 is prevented from rotating relative to the first member 6. Further, the gripping sleeve member 5 is prevented from moving axially relative to the first member 6 when the engagement features 32, 34 of the gripping sleeve member 5 and of the first member 6 are engaged with each other.

The engagement features 32, 34 of the gripping sleeve member 5 and of the first member 6 are configured to be engaged with each other by a snap-fit engagement.

In the following, a dose setting operation and a dose dispense operation is considered for the operable drug delivery device 1 not being engaged with the first or the second attachment 2, 3. To set a dose in the operable drug delivery device 1 not being engaged with any of the attachments 2, 3, the user has to rotate the first member 6, i.e. the dose dial member, relative to the body. Thereby, the dose dial member is concurrently moved in the proximal direction 62 relative to the housing of the operable drug delivery device 1. In order to deliver a dose in the operable drug delivery device 1 not being engaged with any of the attachments 2, 3, the user has to push the dose dial member in the distal direction 4 relative to the housing.

Figure 10:
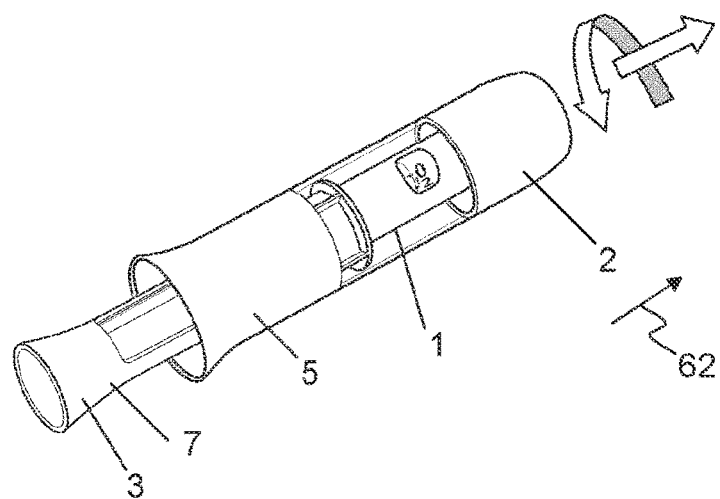
FIG. 10 shows a dose setting operation for the kit shown in FIGS. 7 to 9.

FIG. 10 shows a dose setting operation for a kit comprising the operable drug delivery device 1, the first attachment 2 and the second attachment 3. To set a dose, the user rotates the gripping sleeve member 5 relative to the guarding sleeve member 7. As the first member 6, in this case the dose dial member, is engaged with the gripping sleeve member 5 and the second member 8, i.e. the cartridge holder, is engaged with the guarding sleeve member 7, the first member 6 is thereby rotated relative to the second member 8. Thus, the first member 6 is also moved in the proximal direction 62 relative to the second member 8. Thereby, the gripping sleeve member 5 is moved in the proximal direction relative to the guarding sleeve member 7.

Figure 11:
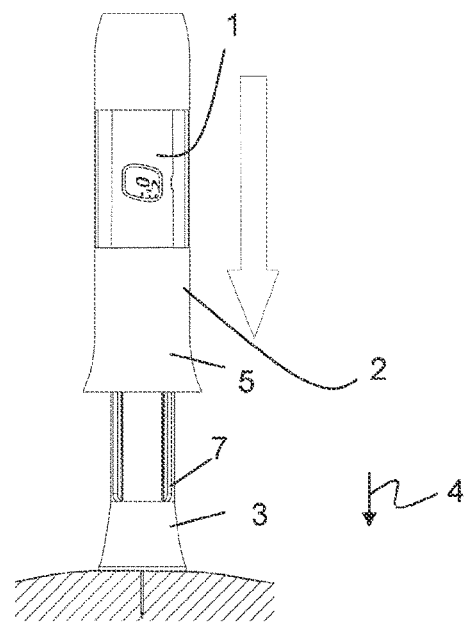
FIG. 11 shows a dose dispense operation for the kit shown in FIGS. 7 to 10.

FIG. 11 shows the dose delivery operation for the kit. To deliver a dose, the gripping sleeve member 5 is moved axially in the distal direction 4 relative to the guarding sleeve member 7. As the gripping sleeve member 5 and the first member 6 are engaged with each other, the axial movement of the gripping sleeve member 5 is transferred into an axial movement of the first member 6 relative to the second member 8 and thus, a dose is delivered.

Figure 12:
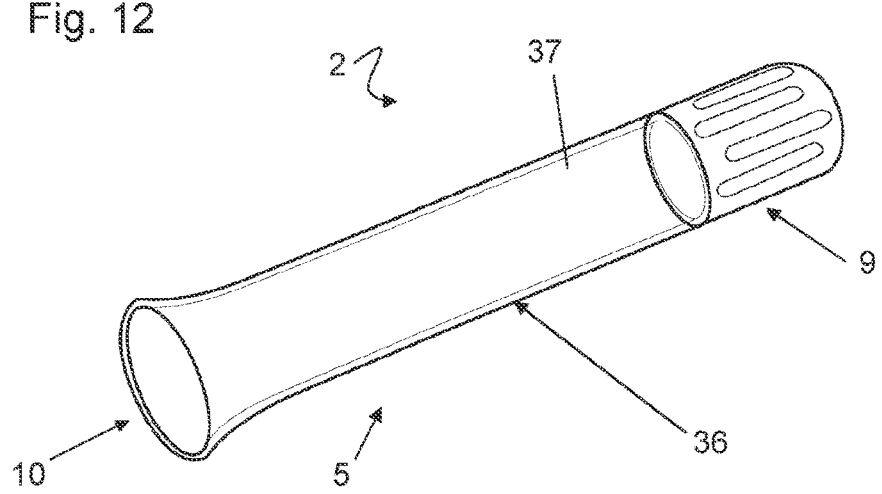
FIG. 12 shows a first attachment according to a second embodiment.

FIG. 12 shows the first attachment 2 according to a second embodiment. According to the second embodiment, the gripping sleeve member 5 comprises the first gripping sleeve member part 9 and a second gripping sleeve member part 36. The first gripping sleeve member part 9 comprises the engagement features 34 (not shown in FIG. 12) at its inner surface. The first gripping sleeve member part 9 is rotatable relative to the second gripping sleeve member part 36. Further, the first gripping sleeve member part 9 is prevented from moving axially relative to the second gripping sleeve member part 36. The second gripping sleeve member part 36 comprises the opening 10 of the gripping sleeve member 5.

The second gripping sleeve member part 36 comprises a first alignment feature 37. The alignment feature 37 comprises a slot at an inner surface of the second gripping sleeve member part 36.

Figure 13:
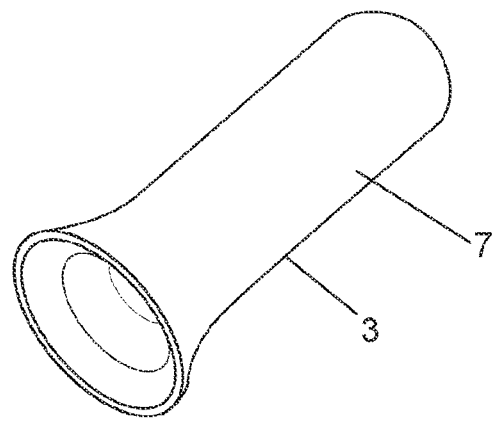
FIG. 13 shows a second attachment according to a second embodiment.

FIG. 13 shows the second attachment 3 comprising the guarding sleeve member 7 according to the second embodiment.

Figure 14:
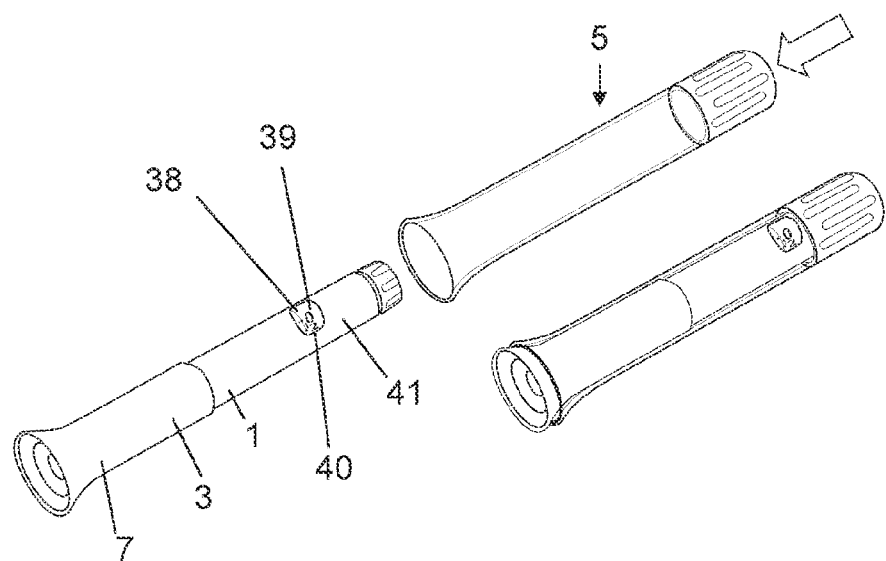
FIG. 14 shows an engagement of a gripping sleeve member with a kit comprising the operable drug delivery device and the second attachment according to the second embodiment.
Figure 15:
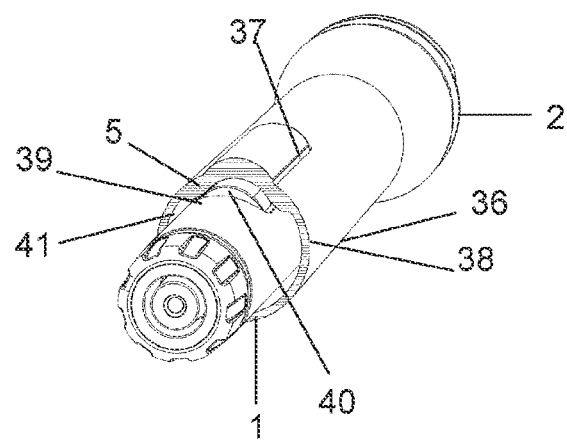
FIG. 15 shows the engagement shown in FIG. 14 from a different perspective.

FIGS. 14 and 15 show an engagement of the gripping sleeve member 5 with a kit comprising the operable drug delivery device 1 and the second attachment 3. The operable drug delivery device 1 comprises a second alignment feature 38. A lens 39 covering the window 40 in the housing 41 of the operable drug delivery device 1 forms a protrusion which forms the second alignment feature 38.

The first alignment feature 37 of the second gripping sleeve member part 36 cooperates with the second alignment feature 38 of the operable drug delivery device 1. When the first and the second alignment features 37, 38 are engaged with each other, an axial movement of the second gripping sleeve member part 36 relative to the housing 41 of the operable drug delivery device 1 is permitted. The first and second alignment feature 37, 38 being engaged with each other prevent a rotation of the second gripping sleeve member part 36 relative to the housing 41 of the operable drug delivery device 1.

In an alternative design, the guarding sleeve member 7 may comprise the second alignment feature 38. In particular, the second alignment feature 38 may be formed by a protrusion of the guarding sleeve member 38 being configured to be engaged with the first alignment feature 37 of the second gripping sleeve member part 36. An engagement of the first alignment feature 37 of the second gripping sleeve member part 36 with the second alignment feature 38 of the guarding sleeve member 7 provides a rotational constrain for the second gripping sleeve member part 36. In particular, thereby, a rotation of the second gripping sleeve member part 36 relative to the guarding sleeve member 7 may be prevented. Further, if the second alignment feature 38 is formed by the guarding sleeve member 7, the lens 39 of the operable drug delivery device 1 is better protected against being damaged by the first alignment feature 37 in case of a misuse.

Figure 16:
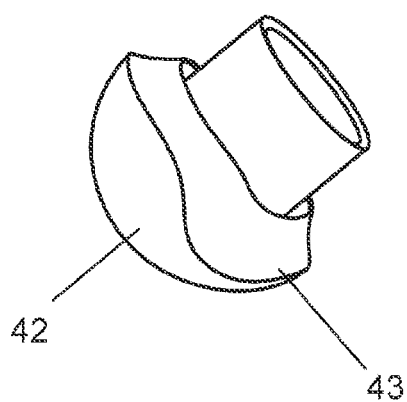
FIG. 16 shows a cap member.
Figure 17A:
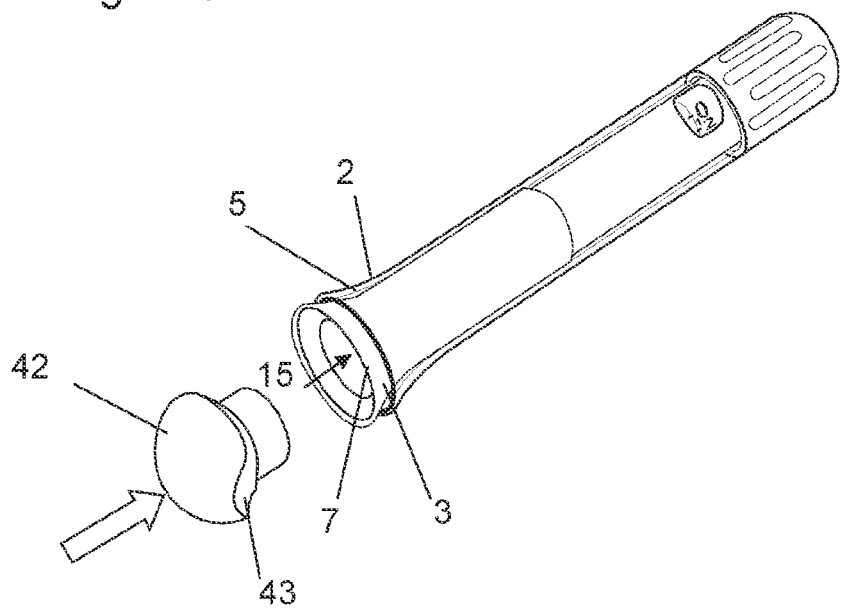
FIG. 17 shows an engagement of the cap member shown in FIG. 16 with the kit according to the second embodiment.
Figure 17B:
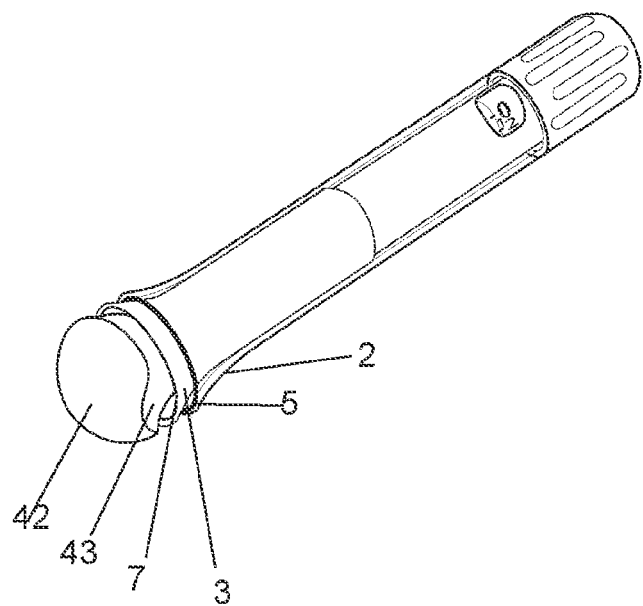

FIG. 16 shows a cap member 42 being engageable to the guarding sleeve member 7. FIG. 17 shows the cap member 42 being engaged to the kit comprising the operable drug delivery device 1, the first attachment 2 and the second attachment 3.

The first opening 15 of the guarding sleeve member 7 defines an opening of the kit at the distal end. The cap member 42 is configured to close the opening 15 by engaging with the guarding sleeve member 7. The cap member 42, the first attachment 2 and the second attachment 3 form a cavity configured to receive the operable drug delivery device 1 such that the operable drug delivery device 1 may be arranged in the cavity. Accordingly, the cap member 42 allows the kit to be transported by a user in the same way as a normal drug delivery device is carried. The cap member 42 has a diameter which is larger than the diameter of the operable drug delivery device 1. Further, the cap member 42 comprises curved edge features 43. The curved edge features 43 allow easily gripping the cap member 42. Accordingly, the cap member 42 can easily be attached to the guarding sleeve member 7 and removed from the guarding sleeve member 7, even by persons with impaired finger dexterity.

Figure 18:
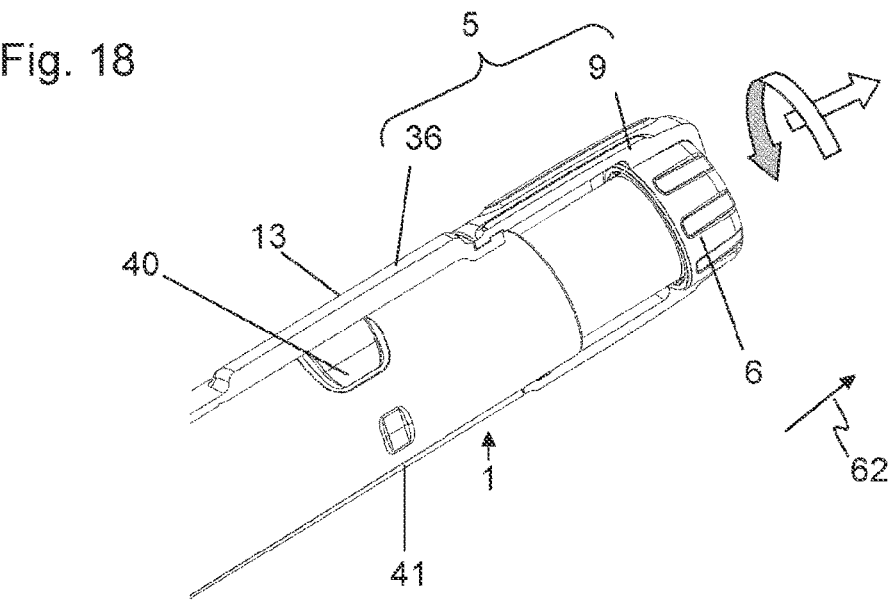
FIG. 18 shows a dose setting operation for the kit according to the second embodiment.
Figure 19:
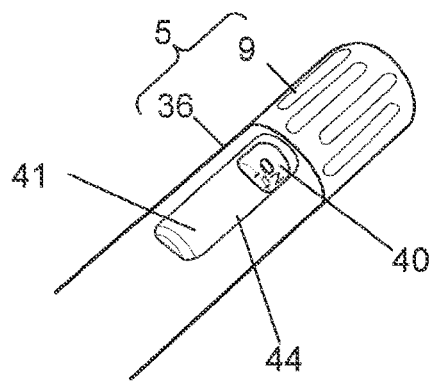
FIG. 19 shows a perspective view of the kit according to the second embodiment before a dose is set.
Figure 20:
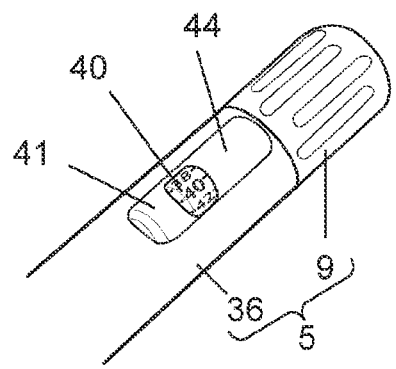
FIG. 20 shows a perspective view of the kit according to the second embodiment after the dose is set.

FIG. 18 shows a dose setting operation in the kit according to the second embodiment. Further, FIG. 19 shows the kit before a dose is set and FIG. 20 shows the kit after the dose is set.

To set a dose, the first gripping sleeve member part 9 is rotated relative to the second gripping sleeve member part 36. The first member 6 of the operable drug delivery device 1, i.e. the dose dial member, is rotationally locked to the first gripping sleeve member part 9. Further, the second gripping sleeve member part 36 is prevented from rotating relative to the housing 41 of the operable drug delivery device 1 due to the engagement of the first and the second alignment feature 37, 38. Accordingly, a rotation of the first gripping sleeve member part 9 relative to the second gripping sleeve member part 36 results in the first member 6 of the operable drug delivery device 1 being rotated relative to the housing 41 of the operable drug delivery device 1. Further, the first member 6 is concurrently to its rotational movement moved axially in the proximal direction 62 relative to the housing 41. Thus, the first gripping sleeve member part 9 also moves axially in the proximal direction 62 relative to the second gripping sleeve member part 36. Moreover, the first gripping sleeve member part 9 moves axially in the proximal direction 62 relative to the housing 41. Furthermore, the first gripping sleeve member part 9 moves axially in the proximal direction 62 relative to the second attachment 3.

During the dose setting operation, the second gripping sleeve member part 36 does not rotate relative to the housing 41 of the operable drug delivery device 1. The second gripping sleeve member part 36 moves out axially in the proximal direction 62 relative to the housing 41 of the operable drug delivery device 1 because the second gripping sleeve member part 36 is connected to the first gripping sleeve member part 9 such that a relative axial movement between the first and the second gripping sleeve member part 9, 36 is prevented. In particular, the second gripping sleeve member part 36 is moved from a first position to a second position relative to the housing 41 wherein the second position is proximal to the first position. The first position corresponds to no dose being set and the second position corresponds to a dose set position.

The second gripping sleeve member part 36 comprises the at least partially transparent part 13 of the gripping sleeve member 5. The at least partially transparent part 13 of the gripping sleeve member 5 overlaps the window 40 in the housing 41 of the operable drug delivery device 1. The at least partially transparent part 13 overlaps the window 40 in each of the first and the second position of the second gripping sleeve member part 36. Alternatively or additionally, a window 44 may be defined in the second gripping sleeve member part 36. Even though the second gripping sleeve member part 36 is moved axially relative to the housing 41 during the dose setting operation, the window 44 in the second gripping sleeve member part 36 remains in overlap with the window 40 in the housing 41 of the operable drug delivery device 1 because the window 44 is designed sufficiently big.

Moreover, during dose setting, the guarding sleeve member 7 moves relative to the gripping sleeve member 5 in the distal direction 4.

Figure 21:
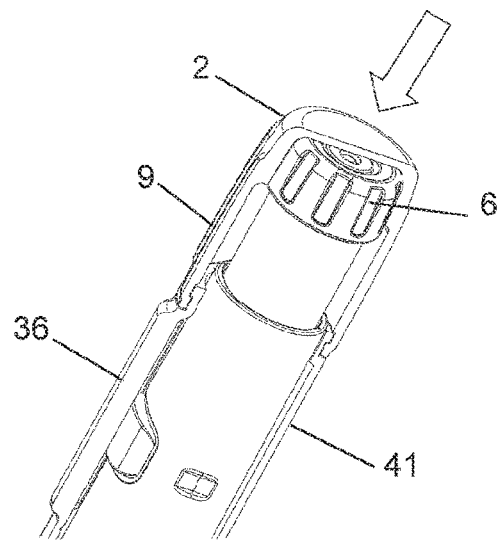
FIG. 21 shows a dose dispense operation for the kit according to the second embodiment.

FIG. 21 shows the kit in a state wherein the dose is set. The first attachment 2 is shown in a cross-sectional view in FIG. 21. In the dose set state, the first member 6 of the operable drug delivery device 1 is arranged in a distance axially away from the housing 41 of the operable drug delivery device 1.

Figure 22:
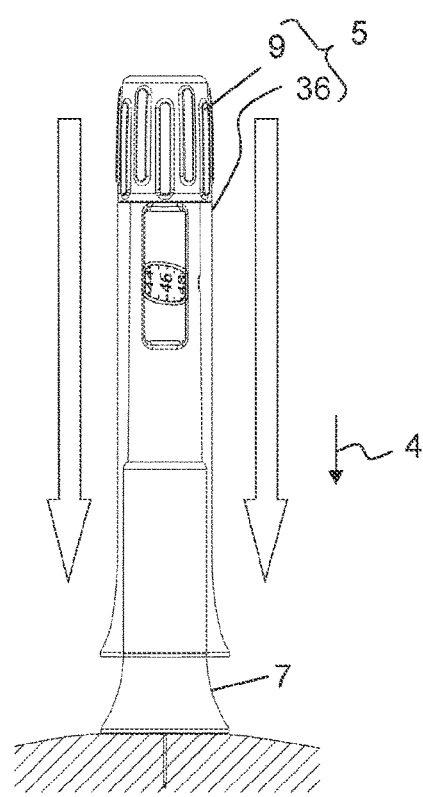
FIG. 22 shows a perspective view of the dose dispense operation for the kit according to the second embodiment.
Figure 23:
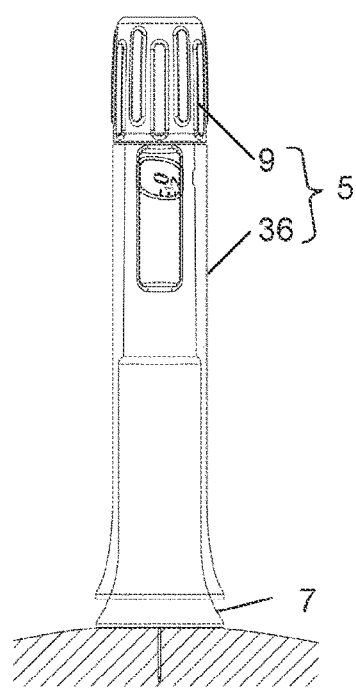
FIG. 23 shows a perspective view of the kit according to the second embodiment after the dose dispense operation is completed.

FIGS. 22 and 23 show a dose dispense operation of the kit. To dispense the dose, the gripping sleeve member 5 is moved axially in the distal direction 4 relative to the guarding sleeve member 7. As the first gripping sleeve member part 9 and the first member 6 are prevented from moved relative to each other, the axial motion of the first gripping sleeve member part 9 is transferred into a movement of the first member 6 and a dose is thereby delivered. The second gripping sleeve member part 36 follows the axial movement of the first gripping sleeve member part 9. In particular, the second gripping sleeve member part 36 does not rotate during the dose dispense operation. Thus, the second gripping sleeve member part 36 can comfortably be held in a full hand grip.

Figure 24:
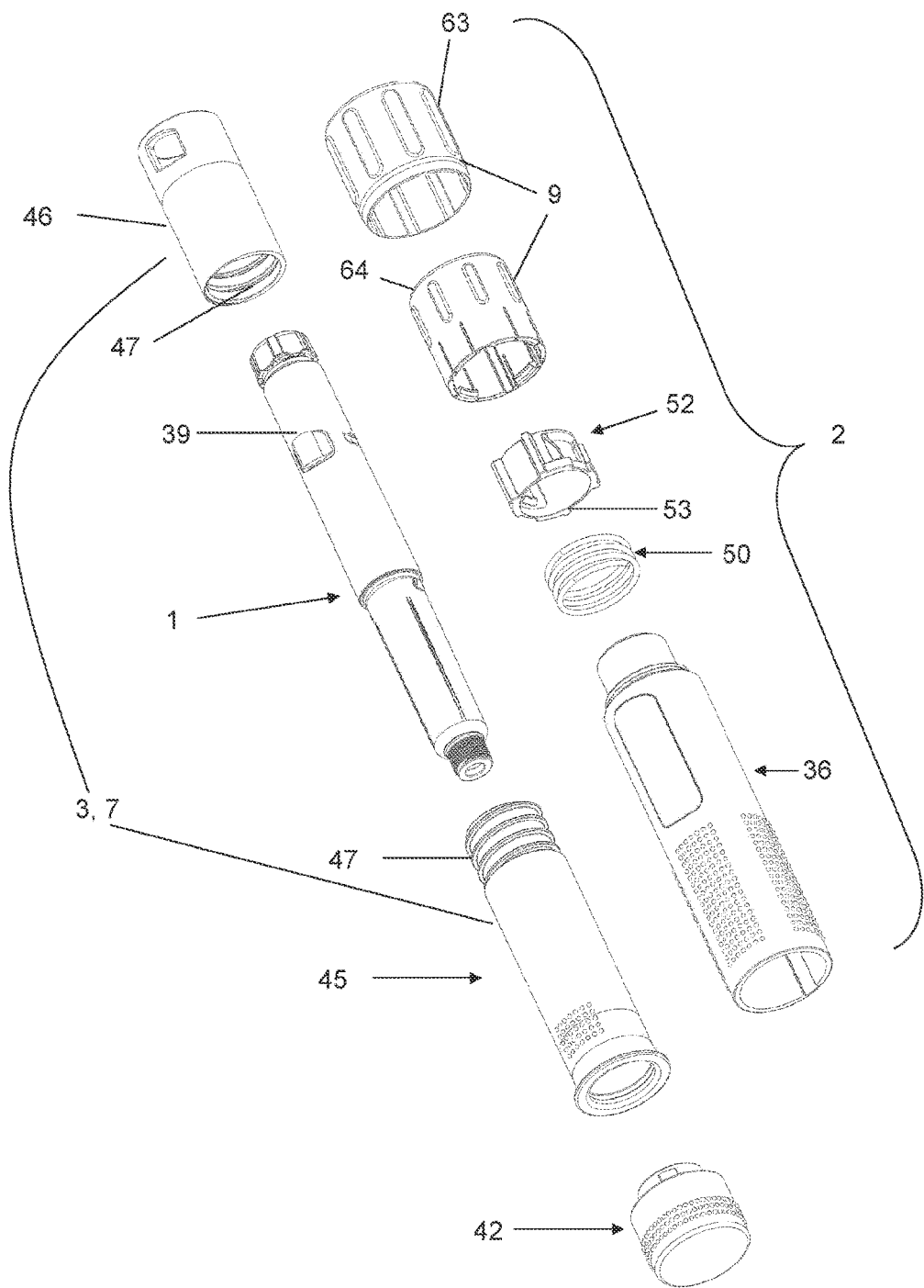
FIG. 24 shows an exploded view of a kit comprising an operable drug delivery device and two attachments according to a third embodiment.

FIG. 24 shows the kit comprising the operable drug delivery device 1 and the two attachments 2, 3 according to a third embodiment. In FIG. 24 the first and the second attachment 2, 3 are shown in an exploded view.

According to the third embodiment, the guarding sleeve member 7 of the second attachment 3 comprises a first guarding sleeve member part 45 and a second guarding sleeve member part 46. The first and the second guarding sleeve member parts 45, 46 each comprised a thread 47 such that the first and the second guarding sleeve member parts 45, 46 are configured to be threadedly engaged with each other.

Figure 25:
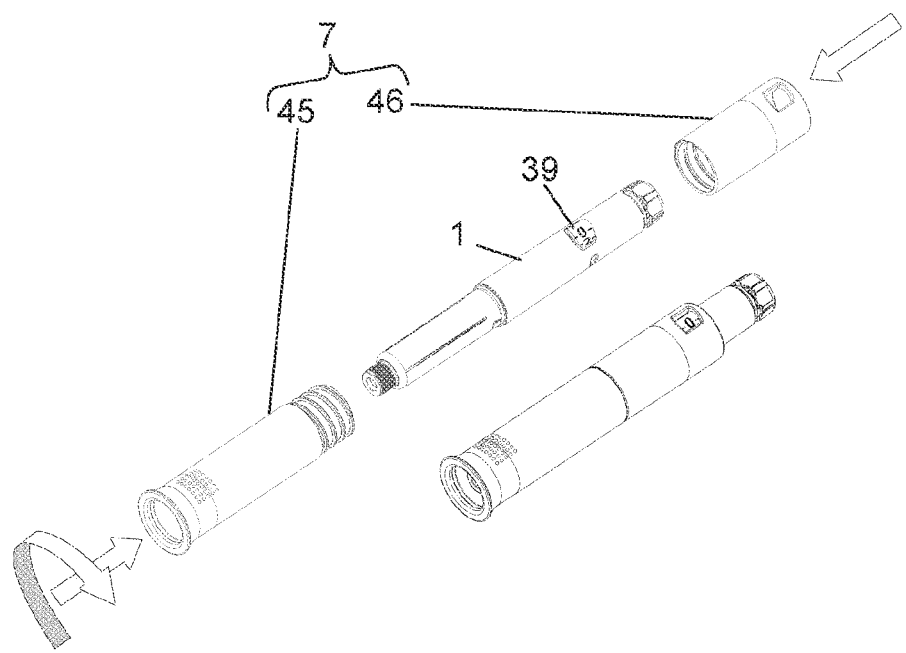
FIG. 25 shows an engagement of a guarding sleeve member according to the third embodiment to the operable drug delivery device.

FIG. 25 shows an engagement of the guarding sleeve member 7 according to the third embodiment to the operable drug delivery device 1. The first and the second guarding sleeve member parts 45, 46 are each be inserted on either side of the operable drug delivery device 1 and than to threadedly engaged with each other. The first and the second guarding sleeve member part 45, 46 are dimensioned such that the guarding sleeve member 7 and the operable drug delivery device 1 are prevented from moving axially relative to each other when the first and the second guarding sleeve member part 45, 46 are engaged with each other.

Further, the second guarding sleeve member part 46 comprises a slot (not shown). The lens 39 of the drug delivery device 1 engages with the slot in the second guarding sleeve member part 46 to restrain a rotational movement of the guarding sleeve member 7 relative to the operable drug delivery device 1 when the first and the second guarding sleeve member parts 45, 46 are engaged with each other.

Alternatively, the third embodiment of the kit may be combined with the guarding sleeve member 7 according to the previous embodiments. This guarding sleeve member 7 consists only of the first guarding sleeve member part 45 which is engageable with the second member 7 by an engagement of the engagement features 20, 25.

Figure 26:
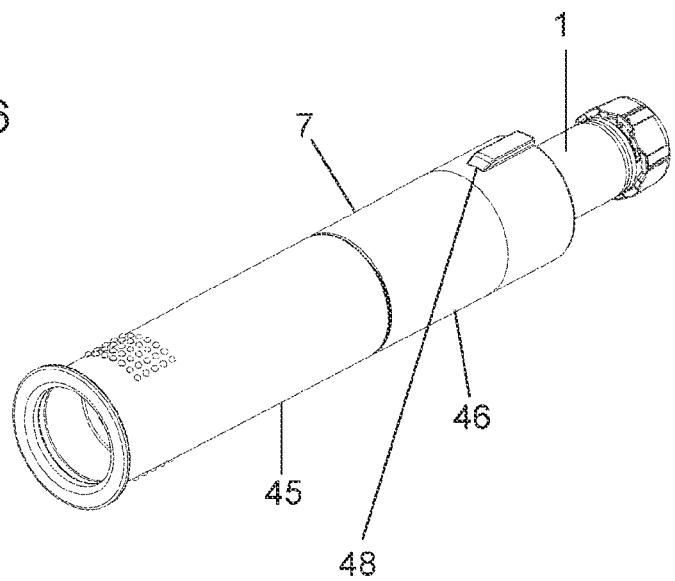
FIG. 26 shows the operable drug delivery device with the guarding sleeve member according to the third embodiment attached.
Figure 27:
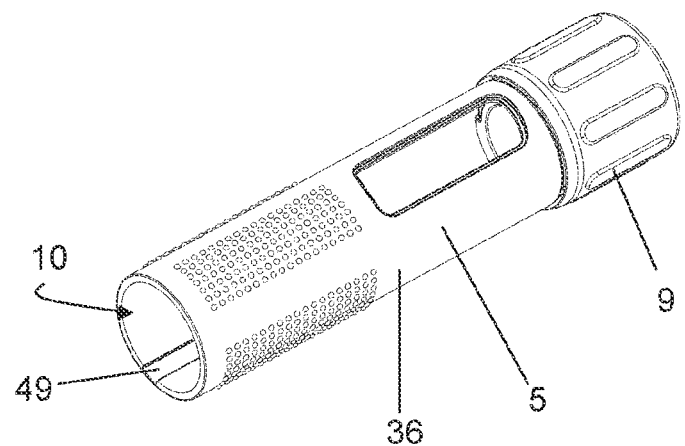
FIG. 27 shows the first attachment according to the third embodiment.

FIG. 26 shows the operable drug delivery device 1 with the guarding sleeve member 7 attached. FIG. 27 shows the first attachment 2 according to the third embodiment.

To assemble the first attachment 2 to the operable drug delivery device 1 with the guarding sleeve member 7 attached, the operable drug delivery device 1 is moved into the opening 10 of the gripping sleeve member 5.

According to the third embodiment, the guarding sleeve member 7 comprises a first orientation member 48. Further, the second gripping sleeve member part 36 comprises a second orientation member 49.

The first orientation member 48 of the guarding sleeve member 7 is a protrusion arranged at an outer surface of the guarding sleeve member 7. The protrusion extends in an axial direction parallel to a longitudinal axis of the guarding sleeve member 7. The second orientation member 49 of the second gripping sleeve member part 36 is a slot arranged at an inner surface of the second gripping sleeve member part 36. The first and the second orientation member 48, 49 are configured to be engageable with each other only when the guarding sleeve member 7 and the second gripping sleeve member part 36 are oriented relative to each other in a predetermined rotational position. Further, an engagement of the first and the second orientation member 48, 49 prevents a relative rotational movement between the guarding sleeve member 7 and the second gripping sleeve member part 36.

FIG. 24 shows the first gripping sleeve member part 9 comprising a button 63 and a button sleeve 64. In an alternative embodiment, the button and the button sleeve may be formed integrally by a single piece.

As shown in FIG. 24, the first attachment 2 further comprises a spring member 50. Further, the first attachment 2 comprises a torque limiting mechanism 51. The torque limiting mechanism 51 defines a maximum allowed torque. The torque limiting mechanism 51 comprises a clutch member 52. In the exploded view of FIG. 24, the clutch member 52 and the spring member 50 are arranged between the first and the second gripping sleeve member part 9, 36. When the first attachment 2 is assembled to the operable drug delivery device, the clutch member 52 abuts an inner surface of the first gripping member part 9 and an outer surface of the first member 6.

The clutch member 52 comprises an engagement feature 53, e.g. a clutch arm. The engagement feature 53 of the clutch member 52 may be configured to engage with the engagement feature 34 of the first member 6 of the operable drug delivery device 1. In particular, the engagement features 53 of the clutch member 52 and of the first member 6 are configured to be connected by a snap-fit connection.

Figure 28:
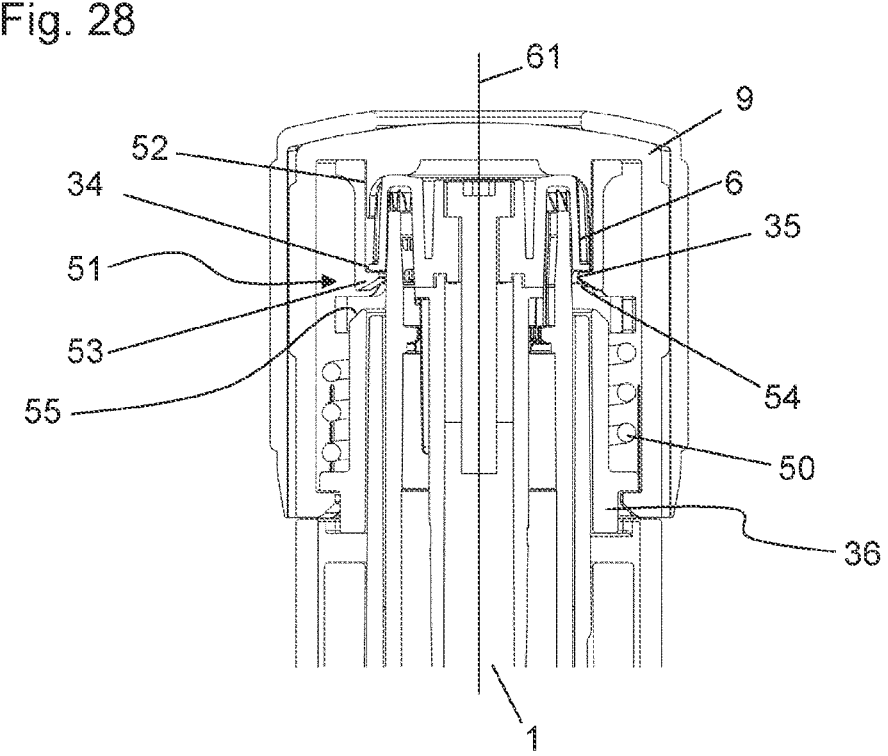
FIG. 28 shows a cross sectional view of the kit according to the third embodiment wherein the first attachment is attached to the operable drug delivery device.

FIG. 28 shows a cross sectional view of the kit according to the third embodiment wherein the first attachment 2 is attached to the operable drug delivery device 1.

To engage the first attachment 2 with the first member 6 of the operable drug delivery device 1, the operable drug delivery device 1 is moved into the opening 10 of the first attachment 2. When the first member 6 abuts the clutch member 52, the first member 6 distorts the engagement feature 53 of the clutch member 52. In particular, the first member 6 moves the engagement features 53 of the clutch member 52 outwards in a direction away from the longitudinal axis 61 of the operable drug delivery device 1. When the first member 6 is moved further in the proximal direction 62 relative to the clutch member 52, the engagement feature 53 of the clutch member 52 engages the engagement feature 34 of the first member 6, thereby preventing a further rotational or axial movement of the first member 6 and the clutch member 52. In particular, the engagement feature 53 of the clutch member 52 snaps into a snap-fit engagement with the engagement feature 34 of the first member 6. When the engagement features 53, 34 of the clutch member 52 and the first member 6 are engaged with each other, the clutch arms are snap fitted into the recess 35 of the first member 6.

The spring member 50 is arranged such that one end of the spring member 50 abuts the clutch member 52 and the other end of the spring member 53 abuts the second gripping sleeve member part 36.

Once the gripping sleeve member 5 is assembled to the operable drug delivery device 1, the spring member 50 exerts a force on the clutch member 52 in a direction away from the second gripping sleeve member part 36, thereby ensuring constant contact between the clutch member 52 and the first member 6.

In contrast to the first and the second embodiment, the third embodiment is configured such that the gripping sleeve member 5 may be disengaged from the first member 6 of the drug delivery device 1 without damaging one of the members of the kit.

Figure 29:
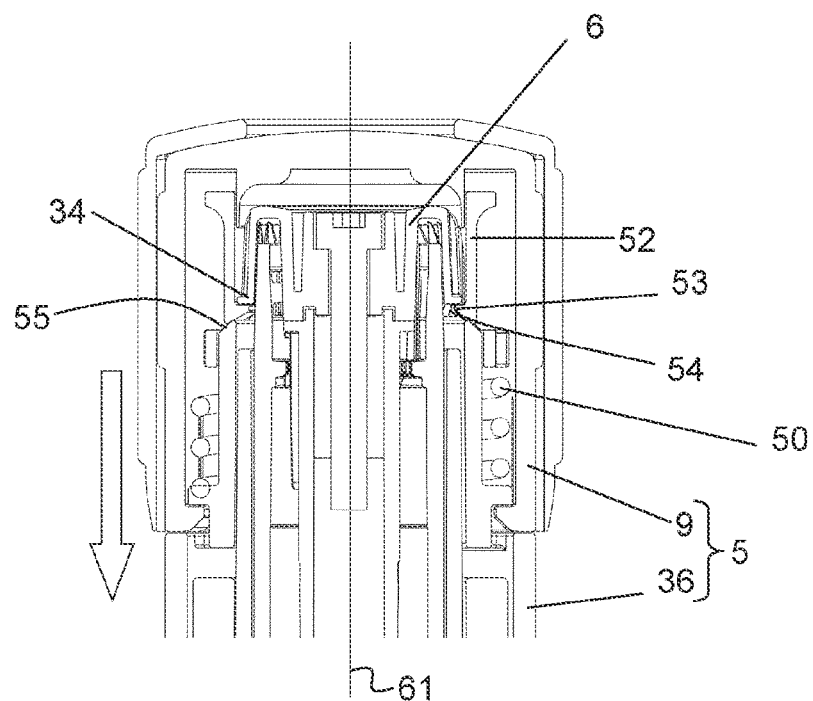
FIG. 29 shows the kit shown in FIG. 28 when a first disengagement feature is moved into its second position.

The first attachment 2 comprises a first disengagement feature 54. The first disengagement feature 54 has a first and a second position. FIG. 28 shows the kit in a state wherein the first disengagement feature 54 is in its first position. FIG. 29 shows the kit when the first disengagement feature 54 is moved into its second position.

The first disengagement feature 54 is a feature of the clutch member 52. In particular, the first disengagement feature 54 is formed by a tapered end face of the engagement feature 53 of the clutch member 52.

However, in an alternative embodiment of the first attachment, the first disengagement feature 54 may be a feature of the first gripping sleeve member part 9. In particular, the first gripping sleeve member part 9 may have a tapered surface forming the first disengagement feature 54.

In the first position of the first disengagement feature 54, the first disengagement feature 54 is configured not to disengage the gripping sleeve member 5 from the first member 6 of the operable drug delivery device 1. The first position corresponds to the engagement feature 53 of the clutch member 52 not being bent outwards in a direction away from the longitudinal axis 61 of the operable drug delivery device 1.

In the second position of the first disengagement feature 54, the first disengagement feature 54 is configured to disengage the gripping sleeve member 5 from the first member 6 of the operable drug delivery device 1. The second position of the first disengagement feature 54 corresponds to the engagement feature 53 of the clutch member 52 being disengaged from the engagement feature 34 of the first member 6. Accordingly, the clutch arms are bent outwards in a radial direction away from the longitudinal axis 61 of the operable drug delivery device 1.

As shown in FIG. 28, the spring member 50 applying a force onto the clutch member 52 in a direction away from the second gripping sleeve member part 36 tends to move the disengagement feature 54 into its first position. To move the first disengagement feature 54 into its second position, the first and the second gripping sleeve member parts 9, 36 have to be moved towards each other overcoming the force applied by the spring member 50.

The second gripping sleeve member part 36 comprises a second disengagement feature 55. The second disengagement feature 55 is formed by a tapered surface of the second gripping sleeve member part 36. The tapered surface is arranged at a distance towards the first disengagement feature 54 in the first position of the first disengagement feature 54.

The second gripping sleeve member part 36 is configured such that an axial movement of the first gripping sleeve member part 9 towards the second gripping sleeve member part 36 engages the second disengagement feature 55 to the first disengagement feature 54, thereby moving the first disengagement feature 54 into its second position. This is shown in FIG. 29.

When the engagement feature 53 of the clutch member 52 is disengaged from the engagement feature 34 of the first member 6, the spring member 50 pushes the clutch member 52 in the proximal direction, thereby moving the first gripping sleeve member part 9 away from the operable drug delivery device 1 and releasing the engagement of the first gripping sleeve member part 9 and the clutch member 52 to the operable drug delivery device 1. Further, the engagement of the second gripping sleeve member part 36 with the operable drug delivery device 1 is also released.

The dose setting and the dose delivery operation are carried out in the same way as described above with respect to the first embodiment.

A dose is set by rotating the first gripping sleeve member part 9 relative to the second gripping sleeve member part 36. During dose setting, the guarding sleeve member 7 moves relative to the gripping sleeve member 5 in the distal direction 4. Due to the engagement of the orientation features 48, 49 between the guarding sleeve member 7 and the second gripping sleeve member part 36, the second gripping sleeve member part 36 and the guarding sleeve member 7 can only move axially relative to each other.

Figure 30:
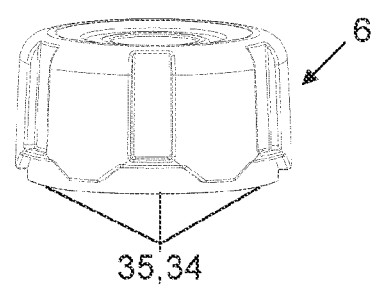
FIG. 30 shows a first member of the operable drug delivery device according to the third embodiment.
Figure 31:
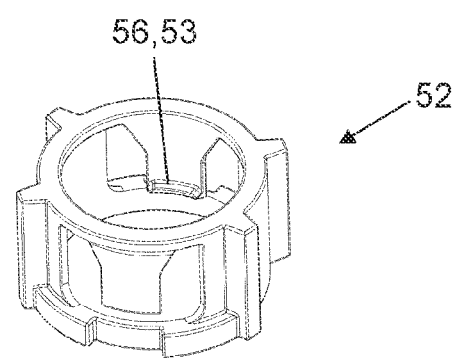
FIG. 31 shows a clutch member.

FIG. 30 shows the first member 6 of the operable drug delivery device 1. FIG. 31 shows the clutch member 52.

When rotating the first gripping sleeve member part 9, the rotation is transmitted from the first gripping sleeve member part 9 to the clutch member 52. The clutch member 52 comprises a projection 56 at its inner surface that is in abutment with the recess 35 of the first member 6 of the operable drug delivery device 1. In particular, the projection 56 of the clutch member 52 fits into the recessed part 35 of the first member 6 enabling a transmission of the rotational movement of the first gripping sleeve member part 9 to the clutch member 52 and then to the first member 6 of the operable drug delivery device 1. Accordingly, the projection 56 of the clutch member 52 corresponds to the engagement feature 53 of the clutch member 52. Further, the recess 35 of the first member 6 corresponds to the engagement feature 34 of the first member 6.

Figure 32:
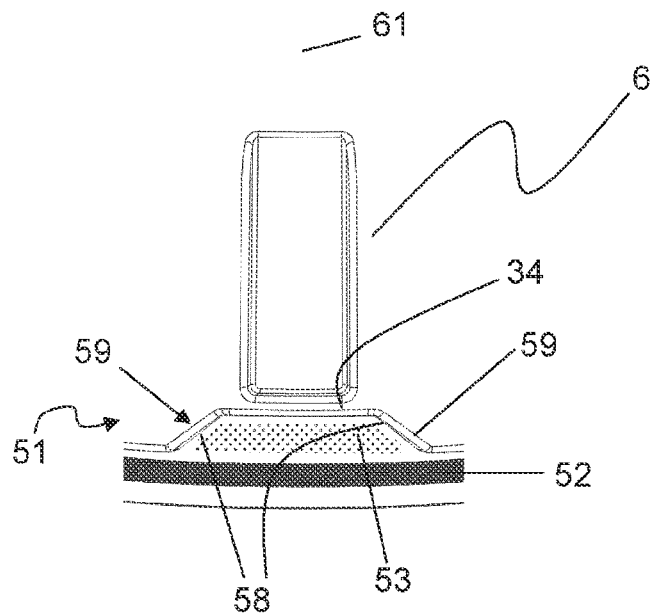
FIG. 32 shows an engagement of the clutch member shown in FIG. 30 with the first member shown in FIG. 31.

FIG. 32 shows an engagement of the engagement feature 53 of the clutch member 52 with the engagement feature 34 of the first member 6.

Each of the engagement feature 53 of the clutch member 52 and the engagement feature 34 of the first member 6 has a face 58, 59 which is arranged in an angle relative to the longitudinal axis of the drug delivery device 1 in the range of 10 to 80° when the first attachment 2 is attached to the operable drug delivery device 1.

If a torque is applied to the first gripping sleeve member part 9, and thereby to the clutch member 52, which is greater than the allowed maximum torque, the tapered faces 58, 59 of the engagement feature 53 of the clutch member 52 and the engagement feature 34 of the first member 6 slide over each other, thereby disengaging the clutch member 52 from the first member 6. Accordingly, in this case, the clutch member 52 is rotated relative to the first member 6. Thus, the number of set doses is not altered as the first member 6 is not moved. Thereby, the torque limiting mechanism 51 prevents a torque being greater than the allowed maximum torque from being applied to the first member 6 of the operable drug delivery device 1.

Figure 33:
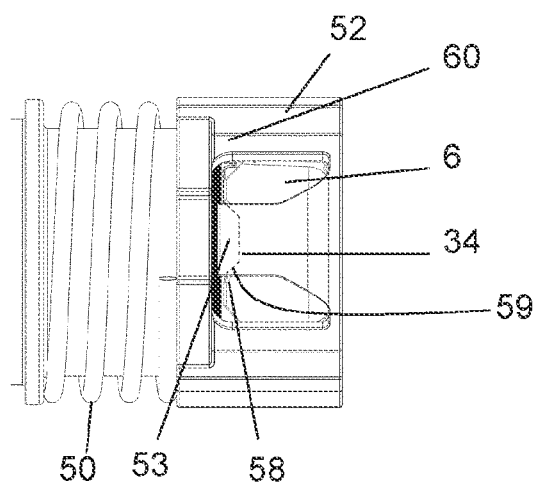
FIG. 33 shows a perspective view of the clutch member and the first member being engaged with each other.
Figure 34:
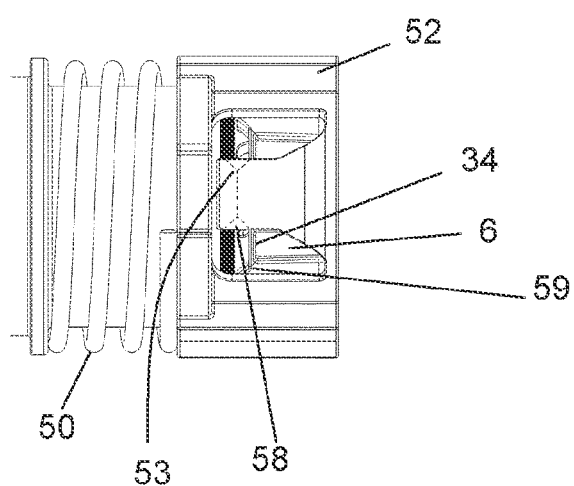
FIG. 34 shows a perspective view of the clutch member and the first member being disengaged from each other.

FIG. 33 shows the clutch member 52 and the first member 6 being engaged with each other. FIG. 34 shows the clutch member 52 and the first member 6 being disengaged from each other.

If the clutch member 52 is rotated in the direction of the input torque and the clutch member 52 is disengaged from the first member 6 by the torque limiting mechanism 51, the tapered faces 58, 59 between the clutch member 52 and the first member 6 force the clutch member 52 further to move axially towards the spring member 50, thereby compressing the spring member 50. Once the clutch member 52 is disengaged from the first member 6, torque is not transmitted to the first member 6 by a rotation of the clutch member 52 until the clutch member 52 reengages with the next engagement feature 60 of the first member 6.

The invention claimed is:

1. An attachment for an operable drug delivery device, comprising a gripping sleeve member that is configured to receive a first member of the operable drug delivery device,
wherein the gripping sleeve member comprises a first gripping sleeve member part comprising a first engagement feature at its inner surface that is configured to engage the first gripping sleeve member part in a torque-proof manner with the first member of the operable drug delivery device and wherein the attachment comprises a torque limiting mechanism defining a maximum allowed torque, wherein the torque limiting mechanism comprises a clutch member configured to slip when a torque greater than the maximum allowed torque is applied to the first gripping sleeve member part.

2. The attachment according to claim 1, wherein the first engagement feature is configured to transfer a movement of the first gripping sleeve member part to a movement of the first member of the operable drug delivery device.

3. The attachment according to claim 1, wherein the first gripping sleeve member part is coupleable with the first member of the operable drug delivery device via the torque limiting mechanism which is configured to prevent a movement of the first gripping sleeve member part being transferred to a movement of the first member if a torque is applied to the first gripping sleeve member part which is greater than the maximum allowed torque.

4. The attachment according to claim 1, wherein the gripping sleeve member comprises an opening for receiving the first member of the operable drug delivery device and
wherein the first engagement feature is arranged at an end of the gripping sleeve member opposite of the opening.

5. The attachment according to claim 1, wherein the first engagement feature is configured to engage the first gripping sleeve member part releasably with the first member of the operable drug delivery device.

6. The attachment according to claim 5, wherein the attachment comprises a spring member providing a spring force tending to move the first gripping sleeve member part into engagement with the first member of the operable drug delivery device.

7. The attachment according to claim 5, wherein the gripping sleeve member comprises a second gripping sleeve member part which is permitted to rotate relative to the first gripping sleeve member part and prevented from moving axially relative to the first gripping sleeve member part.

8. The attachment according to claim 7,
wherein the second gripping sleeve member part comprises a disengagement feature,
wherein the disengagement feature is configured to disengage the releasable engagement of the first gripping sleeve member part with the first member when the first gripping sleeve member part is moved relative to the second gripping sleeve member part.

9. A system of attachments for an operable drug delivery device, comprising an attachment according to claim 7 and further comprising a guarding sleeve member that is configured to be attached to the operable drug delivery device and to receive a second member of the operable drug delivery device.

10. The system according to claim 9,
wherein the guarding sleeve member comprises a first orientation member and the second gripping sleeve member part comprises a second orientation member, and
wherein the first and the second orientation member are configured to be engageable with each other only when the guarding sleeve member and the second gripping sleeve member part are oriented relative to each other in a predetermined relative rotational position.

11. The system according to claim 9, further comprising a cap member which is engageable with the guarding sleeve member and which is configured to close an opening of the guarding sleeve member when engaged with the guarding sleeve member.

12. The system according to claim 9, wherein the gripping sleeve member is configured to at least partly receive the guarding sleeve member.

13. A kit comprising an attachment for an operable drug delivery device or a system of attachments for an operable drug delivery device according to claim 1 and an operable drug delivery device comprising the first member and the second member.

14. The kit according to claim 13, wherein the first member comprises a dose dial member which is configured to be rotated relative to the second member of the operable drug delivery device during a dose setting operation and/or during a dose dispense operation of the operable drug delivery device.

15. The kit according to claim 13, wherein the first member comprises a second engagement feature, and
wherein the second engagement feature of the first member and the first engagement feature of the gripping sleeve member are configured to be connected with each other by a snap-fit connection.

16. A method of improving ergonomics of a drug delivery device comprising:
providing a drug delivery device;
attaching an attachment according to claim 1 to the drug delivery device; and
holding the attachment during administration of a drug.

* * * * *